(12) United States Patent
Toda et al.

(10) Patent No.: US 9,737,573 B2
(45) Date of Patent: Aug. 22, 2017

(54) PREVENTIVE AND/OR AMELIORATIVE AGENT FOR DISEASES, STAMINA ENHANCEMENT AGENT, ANTI-FATIGUE AGENT, AND PHARMACEUTICAL AND FOOD AND DRINK USING THEM

(71) Applicant: TFK Co., Ltd., Kobe-shi, Hyogo (JP)

(72) Inventors: Nobuhiro Toda, Kobe (JP); Yasuhiro Hidaka, Kobe (JP); Masaaki Ishikawa, Sendai (JP); Shuichi Kanno, Sendai (JP)

(73) Assignee: TFK Co., Ltd., Hyogo (JP)

( * ) Notice: Subject to any disclaimer, the term of this patent is extended or adjusted under 35 U.S.C. 154(b) by 177 days.

(21) Appl. No.: 14/444,432

(22) Filed: Jul. 28, 2014

(65) Prior Publication Data
US 2014/0369966 A1  Dec. 18, 2014

Related U.S. Application Data

(62) Division of application No. 13/201,817, filed as application No. PCT/JP2010/070712 on Nov. 19, 2010, now abandoned.

(30) Foreign Application Priority Data

Feb. 16, 2010  (JP) ................................. 2010-031402
Aug. 17, 2010  (JP) ................................. 2010-197119

(51) Int. Cl.
| | | |
|---|---|---|
| *A61K 35/74* | (2015.01) | |
| *A23L 33/00* | (2016.01) | |
| *A23L 33/135* | (2016.01) | |
| *C12N 1/20* | (2006.01) | |
| *C12R 1/00* | (2006.01) | |
| *C12R 1/01* | (2006.01) | |
| *A61K 35/00* | (2006.01) | |

(52) U.S. Cl.
CPC ............ *A61K 35/74* (2013.01); *A23L 33/135* (2016.08); *C12N 1/20* (2013.01); *C12R 1/01* (2013.01); *A61K 2035/11* (2013.01)

(58) Field of Classification Search
None
See application file for complete search history.

(56) References Cited

U.S. PATENT DOCUMENTS

| | | |
|---|---|---|
| 5,530,113 A | 6/1996 | Christ et al. |
| 2003/0039637 A1 | 2/2003 | Toda et al. |
| 2004/0166093 A1 | 8/2004 | Toda et al. |

FOREIGN PATENT DOCUMENTS

| | | |
|---|---|---|
| CN | 1108944 | 9/1995 |
| JP | 8-205819 | 8/1996 |
| JP | 2006-241115 | 9/2006 |
| WO | 01/60977 | 8/2001 |

OTHER PUBLICATIONS

NCBI Blast Nucleotide Sequence at http://blast.ncbi.nlm.nih.gov/Blast.cgi generated on Apr. 14, 2016).*
Woods et al, (Experimental and Molecular Pathology, vol. 74, pp. 282-290; 2003).*
Ranjith et al. (Biotechnology Letters, vol. 29, pp. 1399-1402; 2007).*
Ranjith et al. (Biotechnology Letters, vol. 29, pp. 1399-1402; 2007) (of record).*
Mahadevan et al, The American Journal of Gastroenterology, vol. 97, No. 4, pp. 910-914 (2002).*
Lee et al., International Immunopharmacology, vol. 9, pp. 418-424; 2009.*
Zheng, et al., "The application of antioxidant nutrients in inflammatory bowel disease", Foreign Medical Sciences (Section of Internal Medicine), vol. 23, No. 2, pp. 72-73, 76, 1996—full translation.
Xie, et al., "Research Progress of Antioxidant Selenium", Youjiang Medical Journal, vol. 31, No. 6, pp. 598-600, 2003—full translation.
Zhou, et al., Supply of Se nutrition and athletic ability, Journal of Nanyang Teacher's College, vol. 5, No. 3 pp. 96-98, 2006—English Abstract on p. 98.
Hiraishi, et al., "Molecular Genetic Analyses of *Rhodobacter azotoformans* sp. nov. and Related Species of Phototrophic Bacteria", Systematic and Applied Microbiology, 1996, vol. 19, No. 2, pp. 168-177.
Choudhary, et al., "Genome Analyses of Three Strains of *Rhodobacter sphaeroides*: Evidence of Rapid Evolution of Chromosome II", Journal of Bacteriology, 2007, vol. 189, No. 5, pp. 1914-1921.
Christ, et al., "E5531, a Pure Endotoxin Antagonist of High Potency", Science, 1995, vol. 268, pp. 80-83.
Mullarkey, et al., "Inhibition of Endotoxin Response by E5564, a Novel Toll-Like Receptor 4-Directed Endotoxin Antagonist", The Journal of Pharmacology and Experimental Therapeutics, 2003, vol. 304, No. 3, pp. 1093-1102.
Jagielo, et al., "Grain Dust-Induced Lung Inflammation is Reduced by *Rhodobacter sphaeroids* Diphosphoryl Lipid A", The American Journal of Physiology, vol. 274, No. 1, pp. L26-L31, 1998.
Ranjith, et al., "Rhodethrin: a Novel Indole Terpenoid Ether Produced by *Rhodobacter sphaeroids* has Cytotoxic and Phytohormonal Activities", Biotechnology Letters, vol. 29, No. 9, pp. 1399-1402, 2007.
Tidswell, et al., "Phase 2 Trial of Eritoran Tetrasodium (E5564), a Toll-like Receptor 4 Antagonist, in Patients with Severe Sepsis", Critical Care Medicine, vol. 38, No. 1, pp. 72-83, 2010.

(Continued)

*Primary Examiner* — Soren Harward
*Assistant Examiner* — Paul D. Pyla
(74) *Attorney, Agent, or Firm* — Hamre, Schumann, Mueller & Larson, P.C.

(57) ABSTRACT

A purple non-sulfur bacteria useful in preventing and/or ameliorating at least one disease selected from the group consisting of inflammatory diseases, allergic diseases, and autoimmune diseases and having high safety is provided. A preventive and/or ameliorative agent is for at least one disease selected from the group consisting of inflammatory diseases, allergic diseases, and autoimmune diseases and includes at least one of a purple non-sulfur bacteria and a culture material obtained by culturing the purple non-sulfur bacteria. The purple non-sulfur bacteria includes *Rhodobacter azotoformans*.

1 Claim, 5 Drawing Sheets
(2 of 5 Drawing Sheet(s) Filed in Color)

(56) References Cited

OTHER PUBLICATIONS

Rossignol, et al., "TLR4 Antagonists for Endotoxemia and Beyond", Current Opinion in Investigational Drugs, vol. 6, No. 5, pp. 496-502, 2005.

Wang, "Study on Selenium Transformation by Photosynthetic Bacteria", Shandong University Master's Thesis, 2007, No. 3, 13 pages—including a full English translation.

Uchino, et al., "Green-like and "Red-Like" RubisCO cbbL Genes in *Rhodobacter azotoformans*", Molecular Biology and Evolution, vol. 20, No. 5, pp. 821-830, 2003.

Cantera, et al., "Evolutionary relationship of phototrophic bacteria in the α-*Proteobacteria* based on farnesyl diphosphate synthase", Microbiology, vol. 148, pp. 1923-1929, 2002.

Prepared by TechnoSuruga Laboratory Co., Ltd., Certificate of Base Sequence Data Analysis Report, May 1, 2014, 13 pages—including a partial translation.

\* cited by examiner

PREVENTIVE AND/OR AMELIORATIVE AGENT FOR DISEASES, STAMINA ENHANCEMENT AGENT, ANTI-FATIGUE AGENT, AND PHARMACEUTICAL AND FOOD AND DRINK USING THEM

TECHNICAL FIELD

The present invention relates to a preventive and/or ameliorative agent for diseases, a stamina enhancement agent, and an anti-fatigue agent, a pharmaceutical and a food and drink, using them.

BACKGROUND ART

It is known that the balance in a network of an immune system, a nervous system, an endocrine system, and the like is important for homeostasis in a biological body. It is believed that a cause of develoing diseases such as inflammatory diseases, allergic diseases, autoimmune diseases, cancers, and infectious diseases is a disturbance of the balance in this network. There are various types of fatigue ranging from fatigue associated with serious diseases such as malignant tumors, infectious diseases, and chronic fatigue syndromes to general fatigue caused by mental stresses or physical stresses in daily life.

Conventionally, many preventive and/or ameliorative agents for inflammatory diseases, allergic diseases, autoimmune diseases, and the like, stamina enhancement agents, and anti-fatigue agents have had not only advantageous effects but also adverse effects, whereby it has been difficult to use them for a long term. Therefore, in order to obtain both effectiveness and safety, a preventive and/or ameliorative agent utilizing, for example, *Pleurotus nebrodesis* has been reported (see Patent Document 1, for example).

On the other hand, in order to ameliorate health conditions of non-healthy subjects, a health food utilizing a metabolite obtained by subjecting purple photosynthetic bacteria and lactobacillus to mixed culture have been reported (see Patent Document 2). This health food is superior in efficacy and safety. However, a preventive and/or ameliorative agent, a stamina ameliorative agent, and an anti-fatigue agent in each of which performance is further improved is desired.

PRIOR ART DOCUMENT

Patent Document

Patent Document 1: JP 2006-241115 A
Patent Document 2: WO 2001/60977 A1

SUMMARY OF INVENTION

Problem to be Solved by the Invention

The present invention is intended to provide a preventive and/or ameliorative agent being useful in preventing and/or ameliorating an inflammatory disease, an allergic disease, or an autoimmune disease and having high safety, a stamina enhancement agent, and an anti-fatigue agent.

Means for Solving Problem

In order to achieve the aforementioned object, the preventive and/or ameliorative agent of the present invention is a preventive and/or ameliorative agent for at least one disease selected from the group consisting of inflammatory diseases, allergic diseases, and autoimmune diseases, the preventive and/or ameliorative agent including: at least one of a purple non-sulfur bacteria and a culture material obtained by culturing the purple non-sulfur bacteria, wherein the purple non-sulfur bacteria includes *Rhodobacter azotoformans*.

The stamina enhancement agent and the anti-fatigue agent of the present invention each include: at least one of a purple non-sulfur bacteria and a culture material obtained by culturing the purple non-sulfur bacteria, and the purple non-sulfur bacteria includes *Rhodobacter azotoformans*.

Effects of the Invention

The inventors of the present invention conducted earnest studies in order to achieve the aforementioned object and found out novel purple non-sulfur bacteria having activities of suppressing ulcer formation, suppressing inflammatory cell invasion, suppressing swelling of a mucosal epithelium, regenerating an epithelium, reducing amounts of IgE and histamine in a serum, suppressing Th2 cytokine secretion, ameliorating a Th1/Th2 imbalance, suppressing an allergic reaction, suppressing an autoimmune disease, enhancing stamina, and anti-fatigue. Thus, they reached to the present invention. The purple non-sulfur bacteria of the present invention is useful in preventing and/or ameliorating at least one disease selected from the group consisting of inflammatory diseases, allergic diseases, and autoimmune diseases, enhancing stamina, and anti-fatigue. Moreover, the purple non-sulfur bacteria of the present invention has high safety, so that it can be administered for the purpose of preventing diseases from acquiring, and also, it can be administered for a long term.

BRIEF DESCRIPTION OF DRAWINGS

The patent or application file contains at least one drawing executed in color. Copies of this patent or patent application publication with color drawings will be provided by the Office upon request and payment of the necessary fee FIG. 1A is a photograph (magnification of 32×) of a pathological tissue in Example 2. FIG. 1B is a photograph (magnification of 80×) of the pathological tissue in Example 2.

FIG. 2A is a photograph (magnification of 32×) of a pathological tissue in Comparative Example 1. FIG. 2B is a photograph (magnification of 80×) of the pathological tissue in Comparative Example 1.

FIG. 3A is a photograph (magnification of 32×) of a pathological tissue in Comparative Example 2. FIG. 3B is a photograph (magnification of 80×) of the pathological tissue in Comparative Example 2.

DESCRIPTION OF EMBODIMENTS

Figure 1A:
FIGS. 1A and 1B are the respective photographs of pathological tissues of colon tissue sections in Example 2.

In the preventive and/or ameliorative agent, the stamina enhancement agent, and the anti-fatigue agent of the present invention, *Rhodobacter azotoformans* preferably has the following bacteriological characteristics (1) to (30). The *Rhodobacter azotoformans* having these bacteriological characteristics can be, for example, *Rhodobacter azotoformans* BP0899 strain. The BP0899 strain was deposited with International Patent Organism Depositary, the National Institute of Technology and Evaluation (2-5-8, Kazusakamatari, Kisarazu-shi, Chiba, Japan) under the Accession No. NITE P-644 (deposition date: Sep. 12, 2008) and was internationally deposited under the Accession No. NITE BP-644 (transfer date: Oct. 27, 2010).

(1) cell morphology: a rod shape or an oval shape
(2) polymorphism: negative
(3) cell size: 0.8 μm×1.0 μm
(4) the presence or absence of motility: positive
(5) the presence or absence of spore: negative
(6) luster in nutrient agar culture: positive
(7) pigment production in nutrient agar culture: positive
(8) the presence or absence of surface growth in nutrient broth culture: negative
(9) the presence or absence of medium turbidity in nutrient broth culture: positive
(10) liquefaction of gelatin in gelatin stab culture: negative
(11) coagulation in litmus-milk culture: negative
(12) liquefaction in litmus-milk culture: negative
(13) Gram staining: negative
(14) reduction of nitrate salt: negative
(15) denitrification: positive
(16) MR test: negative
(17) production of indole: negative
(18) generation of hydrogen sulfide: negative
(19) hydrolysis of starch: negative
(20) utilization of citric acid (Christensen): negative
(21) utilization of inorganic nitrogen source (ammonium salt): positive
(22) generation of catalase: positive
(23) generation of oxidase: positive
(24) anaerobic growth: positive
(25) O-F test (oxidation/fermentation): negative/negative
(26) β-galactosidase activity: negative
(27) arginine dihydrolase activity: negative
(28) lysine decarboxylase activity: negative
(29) tryptophan deaminase activity: negative
(30) gelatinase activity: negative In the preventive and/or ameliorative agent, the stamina enhancement agent, and the anti-fatigue agent of the present invention, a base sequence of 16S-rRNA in the *Rhodobacter azotoformans* is preferably a base sequence represented by SEQ ID NO: 1.

A first pharmaceutical of the present invention is a pharmaceutical for preventing and/or ameliorating at least one disease selected from the group consisting of inflammatory diseases, allergic diseases, and autoimmune diseases, the pharmaceutical including: the preventive and/or ameliorative agent of the present invention.

A second pharmaceutical of the present invention includes at least one of the stamina enhancement agent of the present invention and the anti-fatigue agent of the present invention.

First food and drink of the present invention is food and drink, for preventing and/or ameliorating at least one disease selected from the group consisting of inflammatory diseases, allergic diseases, and autoimmune diseases, the food and drink including: the preventive and/or ameliorative agent of the present invention.

Second food and drink of the present invention includes at least one of the stamina enhancement agent of the present invention and the anti-fatigue agent of the present invention.

The purple non-sulfur bacteria of the present invention is *Rhodobacter azotoformans* BP0899 strain (Accession No. NITE BP-644).

A preventive and/or ameliorative method of the present invention is a method for preventing and/or ameliorating at least one disease selected from the group consisting of inflammatory diseases, allergic diseases, and autoimmune diseases, the method including the step of: administering a preventive and/or ameliorative agent containing at least one of a purple non-sulfur bacteria and a culture material obtained by culturing the purple non-sulfur bacteria, wherein the purple non-sulfur bacteria includes *Rhodobacter azotoformans*.

A stamina enhancement method of the present invention is a stamina enhancement method including the step of: administering a stamina enhancement agent containing at least one of a purple non-sulfur bacteria and a culture material obtained by culturing the purple non-sulfur bacteria, wherein the purple non-sulfur bacteria includes *Rhodobacter azotoformans*.

An anti-fatigue method of the present invention is an anti-fatigue method including the step of: administering an anti-fatigue agent containing at least one of a purple non-sulfur bacteria and a culture material obtained by culturing the purple non-sulfur bacteria, wherein the purple non-sulfur bacteria includes *Rhodobacter azotoformans*.

First purple non-sulfur bacteria (*Rhodobacter azotoformans*) or a culture material obtained by culturing the purple non-sulfur bacteria (*Rhodobacter azotoformans*), of the present invention is used for a method for preventing and/or ameliorating at least one disease selected from the group consisting of inflammatory diseases, allergic diseases, and autoimmune diseases.

Second purple non-sulfur bacteria (*Rhodobacter azotoformans*) or a culture material obtained by culturing the purple non-sulfur bacteria (*Rhodobacter azotoformans*), of the present invention is used for at least one of a stamina enhancement method and an anti-fatigue method.

First use of the present invention is the use of a purple non-sulfur bacteria (*Rhodobacter azotoformans*) or a culture material obtained by culturing the purple non-sulfur bacteria (*Rhodobacter azotoformans*), for preventing and/or ameliorating at least one disease selected from the group consisting of inflammatory diseases, allergic diseases, and autoimmune diseases.

Second use of the present invention is the use of a purple non-sulfur bacteria (*Rhodobacter azotoformans*) or a culture material obtained by culturing the purple non-sulfur bacteria (*Rhodobacter azotoformans*), for stamina enhancement or anti-fatigue.

The present invention is described in detail below.

In the present invention, stamina enhancement encompasses, for example, suppression or improvement of decrease in stamina against a physical load. The stamina can be, for example, stamina against activities, and specific examples thereof include stamina against activities such as work and sports and stamina against daily activities.

In the present invention, anti-fatigue means prevention of fatigue symptoms, reduction thereof, recovery therefrom, or amelioration thereof. Examples of fatigue include fatigue from activities such as work and sports, fatigue from daily activities, and fatigue from diseases. The fatigue may encompass malaise.

In the present invention, the stamina enhancement and the anti-fatigue are, in other words, an improvement in physical strength. Specific examples of the improvement in physical strength include maintenance of physical strength, suppression of reduction in physical strength, and improvement in the same.

In the present invention, stamina enhancement effects and anti-fatigue effects may be caused by anti-inflammatory effects of the purple non-sulfur bacteria. The anti-inflammatory effects may be exerted through suppressing expressions of inflammatory cytokine by the purple non-sulfur bacteria. The inflammatory cytokine is not particularly limited, and examples thereof include IL-1 and IFN.

Generally, most conventional anti-fatigue agents have a nutritious supplementary factor. In contrast, the stamina enhancement agent and the anti-fatigue agent of the present invention may be agents of controlling substances causing fatigue by an immunological approach of anti-inflammation, assuming that fatigue is one of inflammatory symptoms.

As mentioned above, the preventive and/or ameliorative agent of the present invention is a preventive and/or ameliorative agent for at least one disease selected from the group consisting of inflammatory diseases, allergic diseases, and autoimmune diseases, the preventive and/or ameliorative agent including: at least one of a purple non-sulfur bacteria and a culture material obtained by culturing the purple non-sulfur bacteria, wherein the purple non-sulfur bacteria includes *Rhodobacter azotoformans*. As mentioned above, the stamina enhancement agent and the anti-fatigue agent of the present invention each includes: at least one of a purple non-sulfur bacteria and a culture material obtained by culturing the purple non-sulfur bacteria, and the purple non-sulfur bacteria includes *Rhodobacter azotoformans*.

<Bacteria>

In the present invention, the *Rhodobacter azotoformans* that is the purple non-sulfur bacteria preferably has the following bacteriological characteristics (1) to (30), as mentioned above. It can be said that the *Rhodobacter azotoformans* having these bacteriological characteristics is, for example, the purple non-sulfur bacteria in the present invention. Specifically, bacteria having these bacteriological characteristics are, as mentioned above, the *Rhodobacter azotoformans* BP0899 strain (Accession No. NITE BP-644), for example.

(1) cell morphology: a rod shape or an oval shape
(2) polymorphism: negative
(3) cell size: 0.8 μm×1.0 μm
(4) the presence or absence of motility: positive
(5) the presence or absence of spore: negative
(6) luster in nutrient agar culture: positive
(7) pigment production in nutrient agar culture: positive
(8) the presence or absence of surface growth in nutrient broth culture: negative
(9) the presence or absence of medium turbidity in nutrient broth culture: positive
(10) liquefaction of gelatin in gelatin stab culture: negative
(11) coagulation in litmus-milk culture: negative
(12) liquefaction in litmus-milk culture: negative
(13) Gram staining: negative
(14) reduction of nitrate salt: negative
(15) denitrification: positive
(16) MR test: negative
(17) production of indole: negative
(18) generation of hydrogen sulfide: negative
(19) hydrolysis of starch: negative
(20) utilization of citric acid (Christensen): negative
(21) utilization of inorganic nitrogen source (ammonium salt): positive
(22) generation of catalase: positive
(23) generation of oxidase: positive
(24) anaerobic growth: positive
(25) O-F test (oxidation/fermentation): negative/negative
(26) β-galactosidase activity: negative
(27) arginine dihydrolase activity: negative
(28) lysine decarboxylase activity: negative
(29) tryptophan deaminase activity: negative
(30) gelatinase activity: negative The purple non-sulfur bacteria further may have properties shown in the following (31) under aerobic culture conditions in the dark. In the following (31), "−" refers to non-production, and "+" refers to production.

(31) Acid production and gas production from saccharide

| Substrate | Acid production/Gas production |
|---|---|
| L-arabinose | −/− |
| D-glucose | −/− |
| D-fructose | −/− |
| maltose | −/− |
| lactose | −/− |
| D-sorbitol | −/− |
| inositol | −/− |
| D-xylose | −/− |
| D-mannose | −/− |
| D-galactose | −/− |
| saccharose | −/− |
| trehalose | −/− |
| glycerin | −/− |

The bacteriological characteristics may be evaluated from the results obtained by main culture after preculture. The preculture may be conducted by inoculating the purple non-sulfur bacteria onto a nutrient agar medium, which is then cultured for 24 hours at 30° C. Conditions of the main culture can be set as appropriate according to the method for evaluating each of the bacteriological characteristics. Specifically, culture conditions for (1) to (5) are, for example, aerobic culture on a nutrient agar medium at 30° C. in the dark. Culture conditions for (6) and (7) are, for example, anaerobic culture in a nutrient broth medium at 30° C. in the light. Culture conditions for (8) to (12) are, for example, aerobic culture in each medium at 30° C. in the dark. Culture conditions for (13), (14), (16), (17), (19) to (23), an oxidation test of (25), (26), (29), (30), and (31) are, for example, aerobic culture in the dark. Culture conditions for (15), (18), (24), a fermentation test of (25), (27), and (28) are, for example, anaerobic culture in the dark. A method for testing each of these bacteriological characteristics is not particularly limited, and a conventionally-known method can be employed. Specific examples thereof include methods described in publications: Barrow G. I. and Feltham R. K. A.: "Cowan and Steel's Manual for the Identification of Medical Bacteria.", 3rd edition, Cambridge University Press, England (1993); SAKAZAKI et al.: "Shin Saikin-baichi-gaku Koza, PART II (The Course of Culturing Medium for Microorganism, PART II)", 2nd edition, Kindai Shuppan, Tokyo (1988); Hasegawa: "Biseibutu no Bunrui to Dotei, PART II (Classification and Determination of Microorganism, PART II)", Gakkai Shuppan Center, Tokyo (1985); and Japanese Society of Soil Micobiology: "Shinpen Dojou-biseibutsu-gaku Jikken (Soil Micoorganism Experimental Method, New Edition)", Yokando, Tokyo (1992). As a method for testing (15), a method of KOMAGATA et al., described in "Biseibutu no Bunrui to Dotei, PART II", a method using a Giltay medium, described in "Shinpen Dojou-biseibutsu-gaku Jikken", or a sewage water testing method using a PYN medium can be employed, for example. In the method of KOMAGATA et al., when growth of the purple non-sulfur bacteria and gas formation are recognized in broth containing 1% sodium nitrate under anaerobic culture conditions, it is determined that denitrification is positive. In the method using a Giltay medium, when a gas is generated in a Giltay medium (pH 7.0 to 7.2) containing a Durham tube, and the Giltay medium turns deep blue in color, under anaerobic culture conditions, it is determined that denitrification is positive. The Giltay medium is a medium obtained by mixing a liquid A (containing 1 g of $KNO_3$, 1 g of asparagine, 5 ml of 1% bromthymol blue-alcohol solution, and 500 ml of distilled water) and a liquid B (containing 8.5 g of sodium citrate, 1 g of $MgSO_4.7H_2O$, 0.05 g of $FeCl_3.6H_2O$, 1 g of $KH_2PO_4$, 0.2 g of $CaCl_2.6H_2O$, and 500 ml of distilled water). In the method for testing each of the bacteriological characteristics, a commercially available bacterial identification kit may be used, for example. The kit is not particularly limited, and for example, a bacterial identification kit API20E (produced by SYSMEX bioMerieux Co., Ltd.) can be used.

The *Rhodobacter azotoformans* further may have the following mycological characteristics (32) to (40):

(32) color of colony: red;
(33) gelatin stab culture: no growth
(34) VP test: negative
(35) utilization of citric acid (Koser): positive
(36) utilization of inorganic nitrogen source (nitrate salt): positive
(37) urease activity: negative
(38) growth pH range: 5 to 9
(39) acid production from D-mannitol: positive
(40) gas production from D-mannitol: negative A method for testing each of these bacteriological characteristics (32) to (40) is not particularly limited and a conventionally-known method can be employed. Specific examples of the method include the methods described in the above-mentioned publications. In the method, a commercially available bacterial identification kit may be used, for example. The kit is not particularly limited, and the above-mentioned bacterial identification kit can be used, for example.

The purple non-sulfur bacteria further may include other purple non-sulfur bacteria besides *Rhodobacter azotoformans*.

The other purple non-sulfur bacteria is not particularly limited, and examples thereof include bacteria of genus *Rhodospirillum*, genus *Rhodocista*, genus *Rhodopila*, genus *Rhodomicrobium*, genus *Blastochloris*, genus *Rhodoplanes*, genus *Rhodobium*, genus *Rhodocyclus*, genus *Rhodoferax*, and genus *Rhodopseudomonas*.

The other purple non-sulfur bacteria may be, for example, bacteria of genus *Rhodobacter* other than the *Rhodobacter azotoformans*.

A source from which the purple non-sulfur bacteria is collected is not particularly limited and examples thereof include the ground, seawater, river water, lake water, and boggy water. The ground is not particularly limited, and examples thereof include a soil, sands, mud, and the like on land, the sea bottom, a river bottom, a lake bottom, and a bog bottom.

A method for isolating the purple non-sulfur bacteria is not particularly limited, and for example, a conventionally-known collection method, culture method, or the like can be used. When the source is lake water, the method may include filtering collected lake water with a filter or the like, culturing a filtrate thus obtained on an agar medium or the like, and isolating the purple non-sulfur bacteria from a colony thus obtained. When the source is mud, the method may include suspending collected mud in a buffer solution or the like, centrifuging this suspended solution thus obtained, culturing a supernatant thus obtained on an agar medium or the like, and isolating the purple non-sulfur bacteria from a colony thus obtained. The purple non-sulfur bacteria thus isolated may be cultured in a liquid medium.

The preventive and/or ameliorative agent, the stamina enhancement agent, and the anti-fatigue agent of the present invention further may contain other bacteria and the like besides the purple non-sulfur bacteria. The other bacteria are not particularly limited, and examples thereof include lactobacillus and yeast. The other bacteria are preferably lactobacillus.

The lactobacillus is not particularly limited, and examples thereof includes *Lactobacillus acidphilus, Lactobacillus casei, Lactobacillus lactis, Lactobacillus bulgaricus, Lactobacillus helveticus, Lactobacillus delbrueckii, Lactobacillus plantarum, Lactobacillus brevis, Lactococcus lactis, Bifidobacterium longum, Bifidobacterium breve, Enterococcus faecalis, Streptococcus thermophilus*, and *Streptococcus lactis*. Preferred examples thereof include *Lactobacillus acidphilus, Lactobacillus bulgaricus, Streptococcus thermophilus*, and *Streptococcus lactis*.

The yeast is not particularly limited, and examples thereof include *Saccharomyces cerevisiae, Saccharomyces carlsbergensis, Saccharomyces ellipsoideus*, and *Saccharomyces rouxii*.

A medium used in culture of a purple non-sulfur bacteria is not particularly limited, and examples thereof include a low-chain fatty acid-containing medium, a maleic acid-containing medium, a medium for reactivating L-dried culture materials of bacteria 802, "Daigo" (manufactured by NIHON PHARMACEUTICAL CO., LTD.), a MYS medium (HIRAISHI and KITAGAWA: Bulletin of the Japanese Society of Scientific Fisheries, vol. 50(11), pp. 1929 to 1937 (1984)), a modified MYS medium, and a growth medium. Preferably, the medium is the low-chain fatty acid-containing medium, the maleic acid-containing medium, or the medium for reactivating L-dried culture materials of bacteria 802, "Daigo" (manufactured by NIHON PHARMACEUTICAL CO., LTD.).

The low-chain fatty acid-containing medium and the maleic acid-containing medium each can be, for example, a medium obtained by containing biotin, Vitamin $B_1$, nicotinic acid, low-chain fatty acid, or a maleic acid sodium salt in a basal medium shown in Table 1 below. The low-chain fatty acid is not particularly limited, and preferred examples thereof include acetic acid, propionic acid, and lactic acid.

TABLE 1

(Basal medium)

| Component | Component concentration (w/v %) |
|---|---|
| $(NH_4)_2SO_4$ | 0.03 |
| $KH_2PO_4$ | 0.05 |
| $MgSO_4 \cdot 7H_2O$ | 0.02 |
| NaCl | 0.05 |
| $NaHCO_3$ | 0.02 |
| Yeast extract | 0.001 |

The modified MYS medium can be, for example, a medium having a composition shown in Table 2 below. The growth medium can be, for example, a medium having a composition shown in Table 3 below.

TABLE 2

(Composition of modified MYS medium)

| Component | Concentration |
|---|---|
| Sodium malate | 3.6 g/l |
| Yeast extract | 0.5 g/l |
| $(NH_4)_2SO_4$ | 1.0 g/l |
| $KH_2PO_4$ | 1.0 g/l |
| $MgCl_2 \cdot 6H_2O$ | 0.2 g/l |
| NaCl | 0.2 g/l |
| $CaCl_2 \cdot 2H_2O$ | 0.045 g/l |
| EDTA-2Na | 2 mg/l |
| $FeSO_4 \cdot 7H_2O$ | 2 mg/l |
| $H_3BO_3$ | 0.1 mg/l |
| $CoCl_2 \cdot 6H_2O$ | 0.1 mg/l |
| $ZnCl_2$ | 0.1 mg/l |
| $MnCl_2 \cdot 4H_2O$ | 0.1 mg/l |
| $Na_2MoO_4 \cdot 2H_2O$ | 0.02 mg/l |
| $NiCl_2 \cdot 6H_2O$ | 0.02 mg/l |
| $CuCl_2 \cdot 2H_2O$ | 0.01 mg/l |
| $Na_2SeO_3$ | 0.001 mg/l |
| Vitamin $B_1$-HCl | 0.5 mg/l |
| Nicotinic acid | 0.5 mg/l |
| p-aminobenzoate | 0.3 mg/l |
| Vitamin $B_{12}$ | 0.05 mg/l |
| Vitamin $B_6$-HCl | 0.1 mg/l |
| Vitamin H | 0.05 mg/l |

TABLE 3

(Composition of growth medium)

| Component | Concentration |
|---|---|
| Sodium acetate | 3 g/l |
| Sodium lactate | 3 g/l |
| Sodium butyrate | 3 g/l |
| Sodium chloride | 5 g/l |
| L-glutamic acid | 0.17 g/l |
| $K_2HPO_4$ | 1 g/l |
| $KH_2PO_4$ | 1.5 g/l |
| EDTA | 20 mg/l |
| $CaCl_2$ | 70 mg/l |
| $H_3BO_3$ | 3 mg/l |
| $CoCl_2 \cdot 6H_2O$ | 0.95 mg/l |
| $ZnSO_4 \cdot 7H_2O$ | 0.24 mg/l |
| $Cu(NO_3)_2 \cdot 3H_2O$ | 0.04 mg/l |
| $NiCl_2 \cdot 6H_2O$ | 0.02 mg/l |
| $MgSO_4 \cdot 7H_2O$ | 0.2 mg/l |
| $MnSO_4 \cdot 5H_2O$ | 2 mg/l |
| $Na_2MoO_4 \cdot 2H_2O$ | 1 mg/l |
| $FeSO_4 \cdot 7H_2O$ | 20 mg/l |
| Biotin | 0.05 mg/l |
| Vitamin$B_1$-HCl | 5 mg/l |

TABLE 3-continued (Composition of growth medium)

| Component | Concentration |
|---|---|
| Nicotinic acid | 5 mg/l |
| Yeast extract | 0.02 g/l |

A temperature range in the culture is not particularly limited, and is, for example, in the range from 23° C. to 39° C., and preferably 30° C.

A pH range in the culture is also not particularly limited, and is, for example, in the range from 5.5 to 8.5, preferably from 6.0 to 8.5, and more preferably 7.0.

The culture may be conducted under aerobic conditions or anaerobic conditions and is not particularly limited. However, it is preferred that the culture is conducted under anaerobic conditions. Light conditions in the culture are also not particularly limited and may be darkness conditions or illuminated conditions. However, it is preferred that the light conditions are conditions under which illuminance is from 2000 to 10000 lux. The culture may be conducted in a sealed and illuminated culture vessel. The culture also may be conducted while stirring a culture solution using a stirrer provided in the sealed and illuminated culture vessel.

Time for the culture is not particularly limited, and may be, for example, time until when growth of the purple non-sulfur bacteria reaches the stationary phase. Under the culture conditions under which growth of the purple non-sulfur bacteria reaches the stationary phase in about 72 hours, the time for the culture may be, for example, 72 hours.

In the culture of the purple non-sulfur bacteria, only the purple non-sulfur bacteria may be cultured, or a mixed culture of the purple non-sulfur bacteria and other bacteria may be conducted, for example. The other bacteria are not particularly limited, and examples thereof include the above-mentioned lactobacillus and the above-mentioned yeast.

As mentioned above, a base sequence of 16S-rRNA in the *Rhodobacter azotoformans* is preferably a base sequence represented by SEQ ID NO: 1. Specifically, the purple non-sulfur bacteria having such a base sequence of 16S-rRNA can be, for example, *Rhodobacter azotoformans* BP0899 strain (Accession No. NITE BP-644).

The base sequence of 16S-rRNA can be identified using a primer and the like after isolating and culturing the purple non-sulfur bacteria and extracting DNA therefrom by the above-mentioned method. As a method for extracting DNA and a method for identifying a base sequence, common methods can be used, and they are not particularly limited. The primer is not particularly limited, and for example, the following primers can be used.

```
(Primer)
9F
                                   (SEQ ID NO: 2)
5'-GAGTTTGATCCTGGCTCAG-3'

339F
                                   (SEQ ID NO: 3)
5'-CTCCTACGGGAGGCAGCAG-3'

785F
                                   (SEQ ID NO: 4)
5'-GGATTAGATACCCTGGTAGTC-3'
```

-continued 1099F
(SEQ ID NO: 5)
5'-GCAACGAGCGCAACCC-3'

536R
(SEQ ID NO: 6)
5'-GTATTACCGCGGCTGCTG-3'

802R
(SEQ ID NO: 7)
5'-TACCAGGGTATCTAATCC-3'

1242R
(SEQ ID NO: 8)
5'-CCATTGTAGCACGTGT-3'

1541R
(SEQ ID NO: 9)
5'-AAGGAGGTGATCCAGCC-3'

It can be said that *Rhodobacter azotoformans* having at least one of the mycological characteristics (1) to (30) and 16S-rRNA having a base sequence represented by SEQ ID NO: 1 is, for example, the purple non-sulfur bacteria of the present invention.

<Culture Material>

Examples of a culture material obtained by culturing the purple non-sulfur bacteria include bacterial cells of the purple non-sulfur bacteria, a culture supernatant of the purple non-sulfur bacteria, and an extract from the bacterial cells of the purple non-sulfur bacteria, and the culture material is not particularly limited. The preventive and/or ameliorative agent, the stamina enhancement agent, and the anti-fatigue agent of the present invention further may contain a culture material obtained by culturing bacteria other than the purple non-sulfur bacteria. The culture material obtained by culturing bacteria other than the purple non-sulfur bacteria is not particularly limited, and examples thereof include bacterial cells of the other bacteria, a culture supernatant of the other bacteria, and an extract from the bacterial cells of the other bacteria. Specific examples of the culture material obtained by culturing bacteria other than the purple non-sulfur bacteria include dried bacterial cells of the lactobacillus and the yeast and extracts therefrom.

Examples of the culture material include a treated material of the bacterial cells, a treated material of the culture supernatant, and a treated material of the extract of the bacterial cells, and the culture material is not particularly limited. The treated materials are not particularly limited, and examples thereof include a substance obtained by concentrating the culture material, a substance obtained by drying the culture material, a substance obtained by freeze-drying the culture material, a substance obtained by treating the culture material with a solvent, a substance obtained by treating the culture material with a surfactant, a substance obtained by treating the culture material with an enzyme, a substance obtained by fractionating proteins of the culture material, a substance obtained by sonicating the culture material, and a substance obtained by disintegrating the culture material. The culture material may be, for example, a mixture of the bacterial cells, the culture supernatant, the extract from the bacterial cells, the treated material of the bacterial cells, the treated material of the culture supernatant, and the treated material of the extract of the bacterial cells. The mixture can be obtained by mixing them in any combination and any ratio and is not particularly limited. The combination is not particularly limited and can be, for example, a mixture of the bacterial cells and the culture supernatant.

The preventive and/or ameliorative agent, the stamina enhancement agent, and the anti-fatigue agent of the present invention further may contain other components such as additives, for example. The additives are not particularly limited and can be, for example, a stabilizing agent and the like. A method for producing each of the preventive and/or ameliorative agent, the stamina enhancement agent, and the anti-fatigue agent is not particularly limited, and a usually-used formulation technology or the like can be employed.

As mentioned above, the preventive and/or ameliorative agent of the present invention is a preventive and/or ameliorative agent for at least one disease selected from the group consisting of inflammatory diseases, allergic diseases, and autoimmune diseases, the preventive and/or ameliorative agent including: at least one of a purple non-sulfur bacteria and a culture material obtained by culturing the purple non-sulfur bacteria. Note here that, in the present invention, preventive and/or ameliorative refers to having at least one of a prevention effect and an amelioration effect. Therefore, the preventive and/or ameliorative agent of the present invention includes a "preventive and ameliorative agent", a "preventive agent", and an "ameliorative agent".

Examples of the inflammatory diseases include inflammatory diseases of internal organs, skins, joints, a central nervous system, and they are not particularly limited. Specific examples thereof include inflammatory bowel diseases such as ulcerative colitis and a Crohn's disease, inflammatory skin diseases such as psoriasis and skin inflammation, encephalitis, hepatitis, nephritis, pneumonia, bronchitis, vasculitis, meningitis, thyroiditis, diabetes, inflammatory bile diseases, and cancers involving inflammations, and they are not particularly limited. Accompanying the exertion of anti-inflammatory effects in preventing and/or ameliorating the inflammatory diseases, effects of relieving pain associated with an inflammation is also exerted.

The allergic diseases are not particularly limited, and examples thereof include Type I allergic diseases, Type II allergic diseases, Type III allergic diseases, Type IV allergic diseases, and Type V allergic diseases. The allergic diseases are preferably the Type I allergic diseases or the Type IV allergic diseases. The Type I allergic diseases are not particularly limited, and specific examples thereof include urticaria, pollinosis, asthma, a PIE syndrome, atopic dermatitis, allergic rhinitis, allergic conjunctivitis, a food allergy, a drug allergy, and anaphylaxis. The Type IV allergic diseases are not particularly limited, and specific examples thereof include contact dermatitis and the like.

The autoimmune diseases are not particularly limited, and examples thereof include rheumatoid arthritis, erythematosus, multiple sclerosis, systemic sclerosis, psoriatic arthritis, an infectious disease, and Sjogren's syndrome.

It is only necessary that the preventive and/or ameliorative agent of the present invention can prevent and/or ameliorate at least one disease of inflammatory diseases, allergic diseases, and autoimmune diseases, and it may prevent and/or ameliorate various diseases. The preventive and/or ameliorative agent of the present invention further may prevent and/or ameliorate other diseases. The other diseases are not particularly limited, and examples thereof include cardiovascular diseases, cancers, and infectious diseases.

The cardiovascular diseases are not particularly limited, and examples thereof include hypertension, myocardial infarction, angina pectoris, and arteriosclerosis.

The cancers are not particularly limited, and examples thereof include a lung cancer, a liver cancer, a gastrointestinal cancer, a renal cancer, a pancreatic cancer, a thyroid cancer, a prostate cancer, an ovarian cancer, an uterine cancer, and a bone cancer.

The infectious diseases are not particularly limited, and examples thereof include infectious diseases caused by various virus such as hepatitis virus, influenza virus, and human immunodeficiency virus and infectious diseases caused by MRSA, hemolytic *streptococcus*, and mycoplasma.

<Pharmaceutical>

The first pharmaceutical of the present invention is not at all limited except that it is for preventing or ameliorating at least one disease selected from the group consisting of inflammatory diseases, allergic diseases, and autoimmune diseases and contains the preventive and/or ameliorative agent of the present invention. The first pharmaceutical of the present invention further may contain at least one of the stamina enhancement agent of the present invention and the anti-fatigue agent of the present invention. The second pharmaceutical of the present invention is not at all limited except that it contains at least one of the stamina enhancement agent of the present invention and the anti-fatigue agent of the present invention. The second pharmaceutical of the present invention further may contain the preventive and/or ameliorative agent of the present invention. Hereinafter, the first pharmaceutical of the present invention and the second pharmaceutical of the present invention are collectively also referred to as merely a "pharmaceutical". In the present invention, the pharmaceutical encompasses a pharmaceutical and a quasi drug. The pharmaceutical of the present invention further may contain other preventive and/or ameliorative agents, other stamina enhancement agents, and other anti-fatigue agents. The other preventive and/or ameliorative agents are not particularly limited, and examples thereof include preventive and/or ameliorative agents for the above-mentioned other diseases. The other stamina enhancement agents and the other anti-fatigue agents are not particularly limited.

Examples of a dosage form of the pharmaceutical include a powder, a fine granule, a granule, a tablet, a coated tablet, a capsule, a troche, and a liquid and it is not particularly limited. A composition of the pharmaceutical is not particularly limited, and the pharmaceutical may contain, besides the preventive and/or ameliorative agent, the stamina enhancement agent, and the anti-fatigue agent, various additives such as a diluent, a binder, a lubricant, a disintegrant, sorbefacient, an emulsifier, a stabilizing agent, and a preservative. The pharmaceutical can be manufactured using a usually-used formulation technology or the like. An animal species into which the pharmaceutical is administered is not particularly limited, and examples thereof include: mammals such as human and inhuman such as monkeys, cattle, pigs, dogs, and cats; bird species such as chickens; and fish and seafood. A method for administering the pharmaceutical is not particularly limited, and examples thereof include oral administration and parenteral administration. Examples of the parenteral administration include percutaneous absorption, an injection, and administration of a suppository. An administration amount of the pharmaceutical can be set as appropriate according to the animal species, ages, and the like. In the preventive and/or ameliorative method, the stamina enhancement method, and the anti-fatigue method of the present invention, an administration method, and an object of the administered are the same as those of the pharmaceutical of the present invention, for example.

<Food and Drink>

The first food and drink of the present invention is not at all limited except that it has a function to prevent and/or ameliorate at least one disease selected from the group consisting of inflammatory diseases, allergic diseases, and autoimmune diseases and contains the preventive and/or ameliorative agent of the present invention. The first food and drink of the present invention further may contain at least one of the stamina enhancement agent of the present invention and the anti-fatigue agent of the present invention. The second food and drink of the present invention is not at all limited except that it contains at least one of the stamina enhancement agent of the present invention and the anti-fatigue agent of the present invention. The second food and drink of the present invention further may contain the preventive and/or ameliorative agent of the present invention. Hereinafter, the first food and drink of the present invention and the second food and drink of the present invention are collectively also referred to as merely "food and drink". In the present invention, food and drink encompasses common food and food with health claims. The common food is not particularly limited, and examples thereof include processed grain products, processed vegetable products, processed fruit products, processed meat products, processed fishery products, dairy products, drinks, and health food. The food and drink of the present invention may contain the preventive and/or ameliorative agent, the stamina enhancement agent, and the anti-fatigue agent as materials or additives, for example. The processed grain products are not particularly limited, and examples thereof include flour, rice flour, cereal bars, senbei (rice crackers), arare (rice cake cubes), and cookies. The processed vegetable products are not particularly limited, and examples thereof include vegetable pastes, dried vegetables, and vegetable soups. The processed fruit products are not particularly limited, and examples thereof include pureed fruits and dried fruits. The processed meat products are not particularly limited, and examples thereof include hams, bacon, and sausages. The processed fishery products are not particularly limited, and examples thereof include tsukudani (foods boiled down in soy sauce), enkanbutsu (salted-dried foods), fish sausages, hanpen (boiled fish paste cake), kamaboko (steamed fish paste cake), and chikuwa (tube-shaped fish paste cake). The dairy products are not particularly limited, and examples thereof include milk beverages, yoghurts, ice creams, and cheeses. The drinks are not particularly limited, and examples thereof include soft drinks, green tea, black tea, and coffee. The food with health claims is generally also called functional food. Examples of the food with health claims include food for specified health use and food with nutrient function claims.

A composition of the food and drink is not particularly limited and can include, for example, various food materials, auxiliary agents, and stabilizing agents besides the preventive and/or ameliorative agent, the stamina enhancement agent, and the anti-fatigue agent. The food and drink can be manufactured using a usually-used formulation technology or the like. An animal species to be an object of the food and drink is not particularly limited, and examples thereof include: mammals such as human and inhuman such as monkeys, cattle, pigs, dogs, and cats; bird species such as chickens; and fish and seafood.

EXAMPLES

Next, the examples of the present invention are described. Note here that the present invention is not limited to the following examples.

Example 1

In the present example, effects of purple non-sulfur bacteria on inflammatory bowel diseases were histologically evaluated using model mice with colitis induced by dextran sulfate sodium (DSS).

(Culture of Bacterial Cell)

First, 0.4% by weight sodium acetate and 5% by weight sucrose were added to a basal medium having the composition shown in Table 4, which then was adjusted to pH 7.0. Thus, a medium for bacterial cell was prepared. The medium for bacterial cell was placed in a sealed and illuminated culture vessel. Then a 20% by volume bacterial suspension of *Rhodobacter azotoformans* BP0899 (Accession No. NITE BP-644) with a bacterial concentration of $1\times10^6$ cells/cm$^3$ was added to the medium, which then was subjected to spinner culture at 30° C. for 7 days. Bacterial cells were collected from a culture solution obtained after the spinner culture using a continuous centrifugal separator (sharpless type). Then the bacterial cells were adjusted to $1\times10^{11}$ cells/cm$^3$ and cryopreserved.

TABLE 4

(Basal medium)

| Component | Component concentration (w/v %) |
|---|---|
| $(NH_4)_2SO_4$ | 0.03 |
| $KH_2PO_4$ | 0.05 |
| $MgSO_4 \cdot 7H_2O$ | 0.02 |
| NaCl | 0.05 |
| $NaHCO_3$ | 0.02 |
| Yeast extract | 0.001 |

(Preperation of Bacterial Cell Powder)

The bacterial cells thus cryopreserved were naturally thawed and then dispensed into suction bottles. The bacterial cells in each of the suction bottles were frozen at −45° C. for 20 minutes using a lyophilizer (manufactured by Takarass Co., Ltd). Thereafter, this suction bottle was connected with a trap that had been cooled to −45° C. and then dried at room temperature (20° C. to 30° C.) and 4 to 6 Pa. Thus, freeze-dried bacterial cells were obtained. The freeze-dried bacterial cells were crashed using a propeller-type crusher (manufactured by Kyoritsu Riko Kabushiki Kaisha) at the number of propeller revolutions of 18000 rpm. Thus, a bacterial cell powder was prepared.

(Test of Administering Feed Containing Bacterial Cell)

In the test of administering feed containing the bacterial cells, 3 of 5-week-old female ICR mice (purchased from Japan SLC, Inc.) were used. For induction of colitis in the mice, a DSS-containing water containing 5 w/v % of dextran sulfate sodium (having the molecular weight from 36000 to 50000, manufactured by ICN biomedicals, Inc.) was prepared. Further, 0.1% by weight of the bacterial cell powder was added to powder feed for feeding mouse ("CF-2", manufactured by CLEA Japan, Inc.), whereby feed containing the bacterial cells was prepared. The mice were caused to ingest water containing no DSS and the feed containing the bacterial cells for 1 week and then caused to ingest the DSS-containing water and the feed containing the bacterial cells for 7 days. Thereafter, on the 8th day after the start of ingesting the DSS-containing water, a colon segment of each of the mice was extirpated.

(Histological Evaluation)

The colon segment thus extirpated was fixed using 10 v/v % of formalin, and a paraffin section was produced by a common method. The paraffin section then was stained with hematoxylin and thereafter histologically observed using an optical microscope. Histological findings of inflammatory cell invasion and swelling of a mucosal epithelium, obtained from the observation were quantified using scores shown in the following table, and then each average value was calculated.

(Score for histological finding)

| Finding | Score |
|---|---|
| Not particular | 0 |
| Slight | 1 |
| Mild | 2 |
| Moderate | 3 |
| Severe | 4 |

Example 2

Water and feed were administered into five 5-week-old female ICR mice (purchased from Japan SLC, Inc.) in the same manner as in Example 1 except that the period of ingesting the water containing no DSS and the feed containing bacterial cells was 4 weeks. Then histological evaluations of ulcer formation and a regenerated epithelium were conducted.

Comparative Example 1

In the present example, 4 of 5-week-old female ICR mice (purchased from Japan SLC, Inc.) were caused to ingest water and feed in the same manner as in Example 1 except that the mice were caused to ingest feed for feeding mouse ("CF-2", manufactured by CLEA Japan, Inc.) containing no purple non-sulfur bacteria as substitute for the feed containing the bacterial cells. Then histological evaluations of ulcer formation, inflammatory cell invasion, swelling of a mucosal epithelium, and a regenerated epithelium were conducted.

Comparative Example 2

In the present example, a 5-week-old female ICR mouse (purchased from Japan SLC, Inc.) was caused to ingest water and feed in the same manner as in Comparative Example 1 except that the water containing no DSS was supplied to the mouse as substitute for the DSS-containing water so that colitis was not induced by DSS in the mouse. Then histological evaluations of ulcer formation, inflammatory cell invasion, swelling of a mucosal epithelium, and a regenerated epithelium were conducted.

The average values of scores for the histological findings of inflammatory cell invasion and swelling of a mucosal epithelium in Example 1 and Comparative Examples 1 and 2 are shown in Table 5 below. As shown in Table 5, it was confirmed that inflammatory cell invasion and swelling of a mucosal epithelium were suppressed in Example 1 as compared with that in Comparative Example 1. Moreover, in Example 1, even though the mice were caused to ingest the feed containing the bacterial cells for 2 weeks, adverse effects were not found.

TABLE 5

| Example | Inflammatory cell invasion | swelling of mucosal epithelium |
|---|---|---|
| Example 1 | 2.33 | 1.00 |
| Comp. Ex. 1 | 2.75 | 1.75 |
| Comp. Ex. 2 | 0.00 | 0.00 |

The average values of scores for the historogical findings of ulcer formation and a regenerated epithelium in Example 2 and Comparative Examples 1 and 2 are shown in Table 6 below. As shown in Table 6, it was confirmed that ulcer formation was suppressed, and regeneration of an epithelium was accelerated in Example 2 as compared with those in Comparative Example 1. It was considered that this result was obtained because the regeneration of an epithelium was accelerated due to the rapid reparing of a ulcer. Moreover, in Example 2, even though the mice were caused to ingest the feed containing the bacterial cells for 5 weeks, adverse effects were not found.

TABLE 6

| Example | Ulcer formation | Regenerated epithelium |
|---|---|---|
| Example 2 | 1.60 | 4.00 |
| Comp. Ex. 1 | 3.00 | 2.75 |
| Comp. Ex. 2 | 0.00 | 0.00 |

Figure 1B:
Figure 2A:
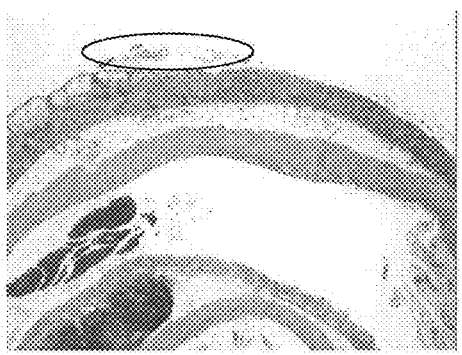
FIGS. 2A and 2B are the respective photographs of pathological tissues of colon tissue sections in Comparative Example 1.
Figure 2B:
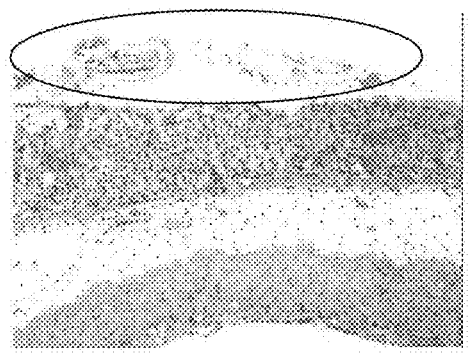
Figure 3A:
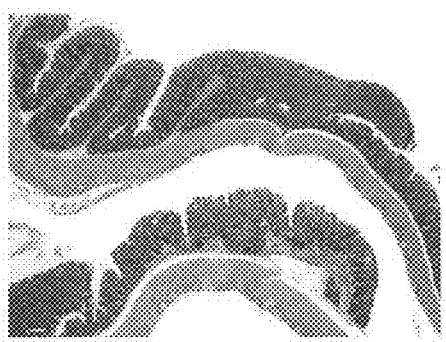
FIGS. 3A and 3B are the respective photographs of pathological tissues of colon tissue sections in Comparative Example 2.
Figure 3B:
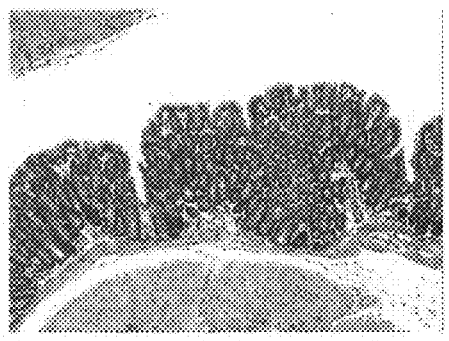

FIGS. 1A to 3B are photopgraphs of pathological tissues in Example 2 and Comparative Examples 1 and 2. FIG. 1A is a photograph (magnification of 32×) of a pathological tissue in Example 2. FIG. 1B is a photograph (magnification of 80×) of the pathological tissue in Example 2. FIG. 2A is a photograph (magnification of 32×) of a pathological tissue in Comparative Example 1. FIG. 2B is a photograph (magnification of 80×) of the pathological tissue in Comparative Example 1. FIG. 3A is a photograph (magnification of 32×) of a pathological tissue in Comparative Example 2. FIG. 3B is a photograph (magnification of 80×) of the pathological tissue in Comparative Example 2.

As shown in FIGS. 1A and 1B, in Example 2 of causing the mice to ingest the feed containing the bacterial cells, ulcer formation was suppressed, and regeneration of an epithelium was accelerated. In the paraffin sections shown in FIGS. 1A and 1B, the histological score for the ulcer formation was 1, and that for the regenerated epithelium was 4. In contrast, as shown in FIGS. 2A and 2B, in Comparative Example 1 of causing the mice to ingest no feed containing bacterial cells, ulcer formation was found on a tissue surface (each part enclosed in ellipse), and regeneration of an epithelium was slightly accelerated. In the paraffin sections shown in FIGS. 2A and 2B, the histological score for the ulcer formation was 4, and that for the regenerated epithelium was 1. As shown in FIGS. 3A and 3B, in Comparative Example 2 of causing the mice to ingest no feed containing the bacterial cells and no DSS-containing water, ulcer formation and regeneration of an epithelium were not found, and the histological score for the ulcer formation and that for the regenerated epithelium were both 0.

Example 3

In the present example, effects of the administration amount of purple non-sulfur bacteria on inflammatory bowel diseases were histologically evaluated using model mice with colitis induced by dextran sulfate sodium (DSS).

(Preparation of Bacterial Cell Powder)

In the present example, a bacterial cell powder was prepared in the same manner as in Example 1.

(Oral Administration Test)

In an oral administration test, 3 groups (2 to 4 mice for each group) of 5-week-old female ICR mice (purchased from Japan SLC, Inc.) were used. For induction of colitis in the mice, a DSS-containing water containing 5 w/v % of dextran sulfate sodium (having the molecular weight from 36000 to 50000, manufactured by ICN biomedicals, Inc.) was prepared. The mice in each of the groups ingested the DSS-containing water ad libitum, and the predetermined amounts (1, 6, and 10 mg/kg, p.o.) of the same bacterial cell powder as in Example 1 were administered into the respective mice once a day for 7 days.

(Histological Evaluation)

Each of extirpated colon segments was fixed using 10 v/v % of formalin, and a paraffin section was produced by a common method. The paraffin section then was stained with hematoxylin and thereafter histologically observed using an optical microscope. Histological findings of ulcer formation, inflammatory cell invasion, swelling of a mucosal epithelium, a regenerated epithelium, and hyperplasia of mucosa were quantified using the same scores as in Example 1. Then the average values in each of the groups were calculated.

Comparative Example 3

In the present example, 3 mice with colitis induced by DSS were caused to ingest the DSS-containing water in the same manner as in Example 3 except that the bacterial cell powder was not orally administered. Then histological evaluations of ulcer formation, inflammatory cell invasion, and a regenerated epithelium were conducted.

Average values of scores for the histological findings of ulcer formation, inflammatory cell invasion, and a regenerated epithelium in Example 3 and Comparative Example 3 were shown in Table 7 below. In Table 7, each number in parentheses indicates the predetermined amount (mg/kg, p.o.) of the bacterial cell powder administered in each group. As shown in Table 7, ulcer formation was suppressed in Example 3 as compared with that in Comparative Example 3. Accompanying the suppression of ulcer formation, formation of a regenerated epithelium also was suppressed. Moreover, it was confirmed in Example 3 that inflammatory cell invasion was suppressed in each of the groups of administering 6 or 10 mg/kg, p.o. of the bacterial cell powder per a day. Moreover, in Example 3, even though 1 to 10 mg/kg, p.o. of the bacterial cell powder was administered for 7 days, adverse effects were not found.

TABLE 7

| Example (Administration amount) | Ulcer formation | Inflammatory cell invasion | regenerated epithelium |
|---|---|---|---|
| Example 3 (1) | 2.50 | 3.00 | 2.00 |
| Example 3 (6) | 0.67 | 2.33 | 0.33 |
| Example 3 (10) | 1.25 | 2.25 | 1.00 |
| Comp. Ex. 3 (0) | 2.67 | 3.00 | 2.67 |

Example 4

In the present example, an oral administration test of a bacterial cell powder prepared in the same manner as in Example 1, using model mice with liver injuries induced by carbon tetrachloride (THC) was conducted as follows, and liver injury prevention effects were evaluated.

In the oral administration test, 3 groups (3 mice for each group) of 5-week-old female ICR mice (purchased from Japan SLC, Inc.) were used. 10 mg/kg, p.o. of the bacterial cell powder was administered in each of the groups once a day for 7 days. Then, in order to induce liver injuries, the predetermined amounts (20, 100 and 500 mg/kg, p.o.) of carbon tetrachloride (THC, manufactured by Wako Pure Chemical Industries, Ltd.) were administered in the respective groups after 24 hours from the last administration of the bacterial cell powder. Subsequently, blood was collected after 24 hours from the administration of THC, and GOT activity (Karmen unit) in the blood was measured. Then an average value of the GOT activity in each of the groups was calculated. As a control, GOT activity in blood was measured in the same manner as for the above-described groups except that the bacterial cell powder and THC were not orally administered. Then an average value of the GOT activity in control was calculated. Then a GOT relative activity value in each of the groups was calculated using the following formula (1).

$$GOT \text{ relative activity value (\%)} = (\text{Average value of } GOT \text{ activity in each group})/(\text{Average value of } GOT \text{ in control}) \times 100 \quad (1)$$

Comparative Example 4

In the present example, an oral administration test was conducted in the same manner as in Example 4 except that the bacterial cell powder was not orally administered.

GOT relative activity values (%) according to the administration amount (mg/kg, p.o.) of THC in Example 4 and Comparative Example 4 are shown in Table 8 below. In Table 8, each of the numbers in parentheses indicates the average value of measured GOT activity values in the blood. As shown in Table 8, the GOT relative activity value in the case where 20 mg/kg, p.o. of THC was administered was 100.3% in Example 4, whereas it was 200.0% in Comparative Example 4. The GOT relative activity value in the case where 100 mg/kg, p.o. of THC was administered was 216.2% in Example 4, whereas it was 435.4% in Comparative Example 4. The GOT relative activity value in the case where 500 mg/kg, p.o. of THC was administered was 311.3% in Example 4, whereas it was 572.4% in Comparative Example 4. That is, GOT activity of Example 4 was suppressed to about ½ compared with that of Comparative Example 4, and liver injury prevention effects were confirmed in Example 4. Moreover, in Example 4, even through 10 mg/kg, p.o. of the bacterial cell powder was administered for 7 days, adverse effects were not found.

TABLE 8

| Example | GOT relative activity value (%) according to administration amount of THC | | |
|---|---|---|---|
| | 20 | 100 | 500 |
| Example 4 | 100.3 (36.5) | 216.2 (78.7) | 311.3 (113.3) |
| Comp. Ex. 4 | 200.0 (66.6) | 435.4 (145.0) | 572.4 (190.6) |

Example 5

In the present example, an oral administration test of a bacterial cell powder prepared in the same manner as in Example 1, using model mice with liver injuries induced by carbon tetrachloride (THC) was conducted as follows, and liver injury prevention effects were evaluated.

In the oral administration test, 3 groups (3 mice for each group) of 5-week-old female ICR mice (purchased from Japan SLC, Inc.) were used. The predetermined amounts (3, 6, and 10 mg/kg, p.o.) of the bacterial cell powder was administered in the respective groups once a day for 7 days. Then, in order to induce liver injuries, the 100 mg/kg, p.o. of carbon tetrachloride (THC, manufactured by Wako Pure Chemical Industries, Ltd.) was administered to each of the groups after 24 hours from the last administration of the bacterial cell powder. Subsequently, blood was collected after 24 hours from the administration of THC, and GOT activity (Karmen unit) in the blood was measured. Then an average value of the GOT activity in each of the groups was calculated. As a control, GOT activity in blood was measured in the same manner as for the above-described groups of administering the bacterial cell powder except that the bacterial cell powder and THC were not orally administered. Then an average value of the GOT activity in control was calculated. Then a GOT relative activity value in each of the groups was calculated in the same manner as in Example 4.

Comparative Example 5

In the present example, an oral administration test was conducted in the same manner as in Example 5 except that 3 of 5-week-old female ICR mice (purchased from Japan SLC, Inc.) were used, and the bacterial cell powder was not orally administered. Then a GOT relative activity value was calculated.

GOT relative activity values (%) according to the respective administration amounts (mg/kg, p.o.) of the bacterial cell powder in Example 5 and a GOT relative activity value (%) in Comparative Example 5 were shown in Table 9 below. In Table 9, each of the numbers in parentheses indicates the average value of measured GOT activity values in the blood. As shown in Table 9, GOT activity was suppressed in each of the groups of administering 3 to 10 mg/kg, p.o. of the bacterial cell powder in Example 5 as compared with that in Comparative Example 5, and liver injury prevention effects were confirmed in Example 5. Moreover, in Example 5, even though 3 to 10 mg/kg, p.o. of the bacterial cell powder was administered for 7 days, adverse effects were not found.

TABLE 9

| Example | GOT relative activity value (%) according to amount of administering bacterial cell powder | | | |
|---|---|---|---|---|
| | 0 | 3 | 6 | 10 |
| Example 5 | — | 333.8 (121.5) | 375.8 (136.8) | 216.2 (78.7) |
| Comp. Ex. 5 | 398.4 (145.0) | — | — | — |
| Control | 100.0 (36.4) | — | — | — |

Example 6

In the present example, an oral administration test of a bacterial cell powder prepared in the same manner as in Example 1, using model mice with liver injuries induced by carbon tetrachloride (THC) was conducted as follows. Then effects of the bacterial cell powder were histologically evaluated.

(Oral Administration Test Using Model Mice with Induced Liver Injuries)

In the present example, an oral administration test was conducted in the same manner as in Example 4 except that 10 mg/kg, p.o. of the bacterial cell powder was administered once a day for 1 day or 7 days, and 100 mg/kg, p.o. of carbon tetrachloride (THC, manufactured by Wako Pure Chemical Industries, Ltd.) was administered after 24 hours from the last administration of the bacterial cell powder. As a control, a group (3 mice) of orally administering no bacterial cell powder and the THC was used.

(Histological Evaluation)

Each of livers was extirpated after 24 hours from the administration of THC. The liver thus extirpated was fixed using 10 v/v % of formalin, and a paraffin section was produced by a common method. The paraffin section was stained with hematoxylin and thereafter histologically observed using an optical microscope. Histological findings of centrilobular hepatic necrosis and inflammatory cell invasion in the liver were quantified using the same scores as in Example 1. Then average values in each of the groups and control were calculated.

Comparative Example 6

In the present example, an oral administration test was conducted in the same manner as in Example 6 except that the bacterial cell powder was not orally administered. Then histological evaluations of centrilobular hepatic necrosis and inflammatory cell invasion in livers were conducted.

Average values of scores for hitological findings of the centrilobular hepatic necrosis and the inflammatory cell invasion in the livers of Example 6 and Comparative Example 6 are shown in Table 10 below. In Table 10, each of numbers in parentheses indicates the number of days for which the bacterial cell powder is administered (hereinafter referred to as "administration days of the bacterial cell powder). As shown in Table 10, the centrilobular hepatic necrosis and the inflammatory cell invasion were suppressed in Example 6 as compared with those in Comparative Example 6. That is, liver injuries induced by THC were suppressed by the oral administration of the bacterial cell powder. Moreover, in Example 6, even though 10 mg/kg, p.o. of the bacterial cell power was administered from 1 to 7 days, adverse effects were not found.

TABLE 10

| Example (administration days) | hepatic necrosis | Inflammatory cell invasion |
|---|---|---|
| Example 6 (1 day) | 2.00 | 1.00 |
| Example 6 (7 days) | 1.00 | 0.50 |
| Comp. Ex. 6 | 3.33 | 1.33 |
| Control | 0.00 | 1.00 |

Example 7

In the present example, an oral administration test of a bacterial cell powder prepared in the same manner as in Example 1, using model mice with allergic reactions caused by egg albumin was conducted as follows. Then effects of the bacterial cell powder on a Th1/Th2 balance in the allergic reactions caused by egg albumin were evaluated.

(Measurement of IgE in Serum)

First, 2 mg of egg albumin (grade V, produced by Sigma-Aldrich Corporation) was dissolved in 0.2 ml of saline solution. Then 2 mg of aluminum hydroxide gel (No. 019-19501, Lot. WKJ 4431, produced by Wako Pure Chemical Industries, Ltd.) was added and suspended in the resultant solution. Thus, an egg albumin/aluminum hydroxide gel was prepared. In the oral administration test, 5 of 4-week-old female BALB/c mice (purchased from Japan SLC, Inc.) were used. 10 mg/kg, p.o. of the bacterial cell powder was administered into each of the mice once a day for 2 weeks. Then, on the last day of administering the bacterial cell powder, the egg albumin/aluminum hydroxide gel was administered into an abdominal cavity of each of the mice. Further, each of the mice was given a booster immunization after 10 days from the last day, and then blood was collected after 1 week from the booster immunization. Sera were collected from the collected blood, and then amounts of IgE in the sera were measured in accordance with a protocol of ELISA Kit (produced by Bethyl Laboratories). Then an average value of the amounts of IgE in the 5 mice was calculated.

(Measurement of Amount of IL-4 in Serum)

In this measurement, the bacterial cell powder was administered, an egg albumin/aluminum hydroxide gel was prepared and administered, and blood was collected in the same manner as in the measurement of the amount of IgE in a serum, except that 2 of 4-week-old female BALB/c mice (purchased from Japan SLC, Inc.) were used. Sera were collected from the blood thus collected, and then amounts of IL-4 in the sera were measured in accordance with a protocol of IL-4, mouse, ELISA Kit (96 wells, produced by Bethyl Laboratories). Then an average value of the amounts of IL-4 in the 2 mice was calculated.

(Measurement of Amount of Cytokine in Culture Supernatant of Spleen Cells)

In this measurement, the bacterial cell powder was administered, and an egg albumin/aluminum hydroxide gel was prepared and administered in the same manner as in the measurement of the amount of IgE in a serum except that 3 of 4-week-old female BALB/c mice (purchased from Japan SLC, Inc.) were used. Each of spleens was collected after 1 week from a booster immunization. Spleen cells were collected from each of the spleens, and the spleen cells thus collected were suspended in an RPMI 1640 medium (produced by Gibco Laboratories) containing 100 μg/ml of egg albumin so that the resultant medium had a density of $5 \times 10^6$ cells/ml. Then the spleen cells were cultured under the conditions of 95% of air and 5% of carbon dioxide concentration at 37° C. for 3 days. After the culture, a culture supernatant was collected, and amounts of IFN-γ, IL-2, IL-4, and IL-5 in the culture supernatant were measured in accordance with a protocol of each ELISA Kit (produced by Bethyl Laboratories) shown Table 11 below. Then each average value of 3 mice was calculated.

TABLE 11

| (ELISA Kit) | |
|---|---|
| Cytokine | Kit name |
| IFN-γ | IFN-γ, mouse, ELISA, Quantitation Kit |
| IL-2 | IL-2, mouse, ELISA Kit |
| IL-4 | IL-4, mouse, ELISA Kit |
| IL-5 | IL-5, mouse, ELISA Kit |

Comparative Example 7

In the present example, an oral administration test was conducted in the same manner as in Example 7 except that the bacterial cell powder was not orally administered. Then amounts of IgE and IL-4 in a serum were measured, and amounts of IFN-γ, IL-2, IL-4, and IL-5 in a culture supernatant of spleen cells were measured. Then each average value was calculated.

An average value of the amounts of IgE in sera of Example 7 and that of Comparative Example 7 are shown in Table 12 below. As shown in Table 12, the amounts of IgE were reduced in Example 7 of administering the bacterial cell powder as compared with those in Comparative Example 7 of administering no bacterial cell powder.

TABLE 12

| Example | IgE amount (U/ml) |
| --- | --- |
| Example 7 | 40.1 |
| Comp. Ex. 7 | 64.0 |

Measurement results of amounts of IL-4 in sera of Example 7 and those of Comparative example 7 are shown in Table 13 below. As shown in Table 13, the amounts of IL-4 were reduced in Example 7 of administering the bacterial cell powder as compared with that in Comparative Example 7 of administration no bacterial cell powder. That is, an increase in amount of IL-4 that is Th2 cytokine was suppressed, and further, as mentioned above, an increase in amount of IgE was suppressed. Thus, it was suggested that the bacterial cell powder ameliorates a Th1/Th2 imbalance evoking allergic reactions through suppressing secretion of Th2 cytokine.

TABLE 13

| Example | IL-4 amount (pg/ml) |
| --- | --- |
| Example 7 | 55.7 |
| Comp. Ex. 7 | 90.6 |

Measurement results of amounts of IFN-γ, IL-2, IL-4, and IL-5 in the culture supernatant of Example 7 and those of Comparative Example 7 are shown in Table 14 below. As shown in Table 14, amounts of IFN-γ and IL-2, being Th1 cytokine were increased, and amounts of IL-4 and IL-5, being Th2 cytokine were reduced in Example 7 of administering the bacterial cell powder as compared with those in Comparative Example 7 of administration no bacterial cell powder. That is, since allergic reactions are evoked when Th2 is dominant, it was suggested that the bacterial cell powder ameliorates a Th1/Th2 imbalance and exerts anti-allergic properties by suppressing secretion of Th2 cytokine. Moreover, in Example 7, even though 10 mg/kg, p.o. of bacterial cell powder was administered once a day for 2 weeks, adverse effects were not found.

TABLE 14

| Example | IFN-γ (ng/ml) | IL-2 (pg/ml) | IL-4 (pg/ml) | IL-5 (pg/ml) |
| --- | --- | --- | --- | --- |
| Example 7 | 7.9 | 661.8 | 74.0 | 873.3 |
| Comp. Ex. 7 | 5.3 | 255.5 | 146.6 | 1685.4 |

Example 8

In the present example, an oral administration test of the bacterial cell powder prepared in the same manner as in Example 1, using mice with inflammations in situ thereof (edema) evoked by egg albumin was conducted as follows. Then anti-allergic properties were evaluated.

First, an egg albumin/aluminum hydroxide gel was prepared in the same manner as in Example 7 except that an administration amount of egg albumin (grade V, produced by Sigma-Aldrich Corporation) was 20 μg. The bacterial cell powder and the egg albumin/aluminum hydroxide gel were administered into each of the mice in the same manner as in Example 7 except that 6 of 4-week-old female BALB/c mice (purchased from Japan SLC, Inc.) were used. 20 μL of the egg albumin/aluminum hydroxide gel were inoculated into each of footpads of the mice after 10 days from the last day of administering the bacterial cell powder. Volumes of edemas generated on the respective footpads were measured using Volume Meter MK-550 (produced by MUROMACHI KIKAI CO., LTD.) after 24 hours from the inoculation. Then an average value of the volumes was calculated.

Comparative Example 8-1

In the present example, an oral administration test was conducted in the same manner as in Example 8 except that 3 of the mice were used as an untreated group, and the bacterial cell powder and the egg albumin/aluminum hydroxide gel were not administered. Then volumes of edemas generated on the respective footpads were measured, and an average value of the volumes was calculated.

Comparative Example 8-2

In the present example, as a group of administering no bacterial cell, an oral administration test was conducted in the same manner as in Example 8 except that the bacterial cell powder was not orally administered. Then volumes of edemas generated on the respective footpads were measured, and an average value of the volumes was calculated.

Figure 4:
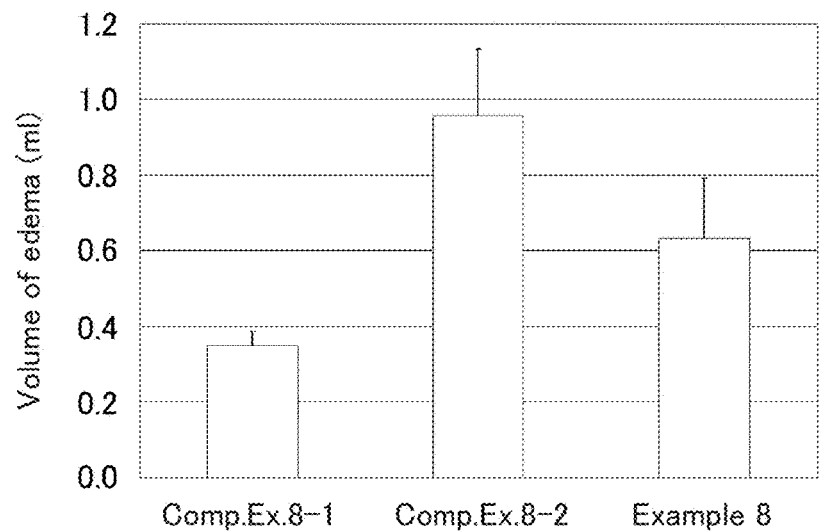
FIG. 4 is a graph showing the respective average values of volumes of edema in Example 8 and Comparative Examples 8-1 and 8-2.
Figure 5:
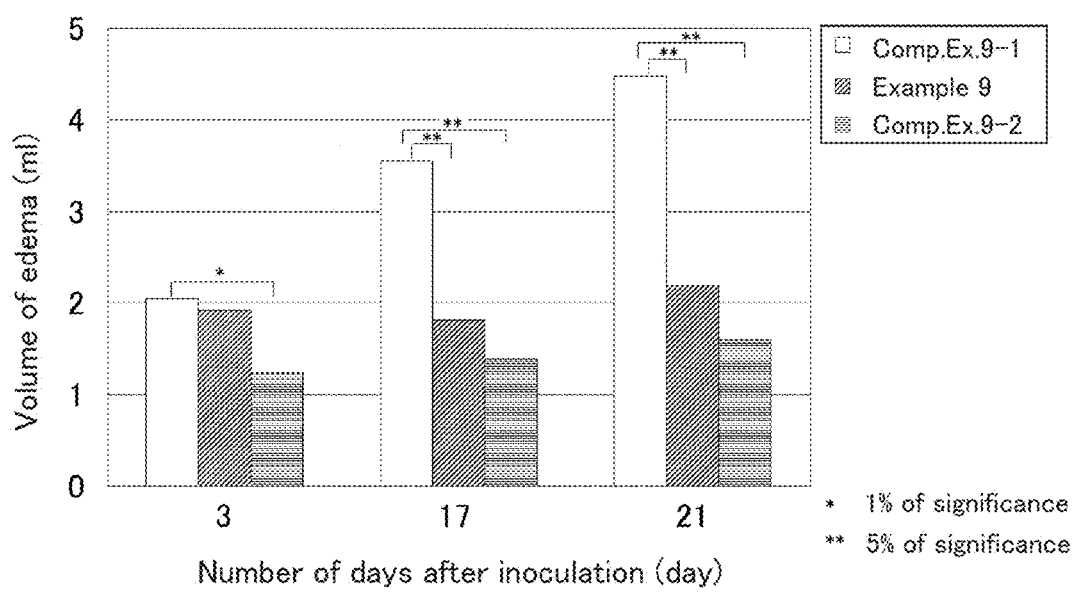
FIG. 5 is a graph showing the respective average values of volumes of edema in Example 9 and Comparative Examples 9-1 and 9-2.
Figure 6A:
FIG. 6A is soft X-ray photographs of hind limbs in Example 9.
Figure 6B:
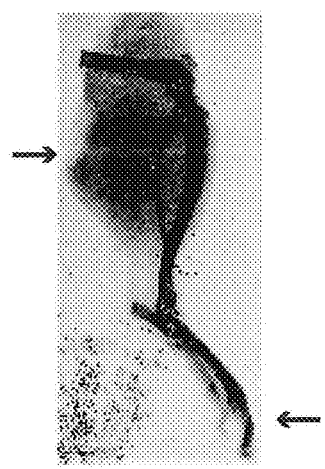
FIG. 6B is a soft X-ray photograph of a hind limb in Comparative Example 9-1.
Figure 6C:
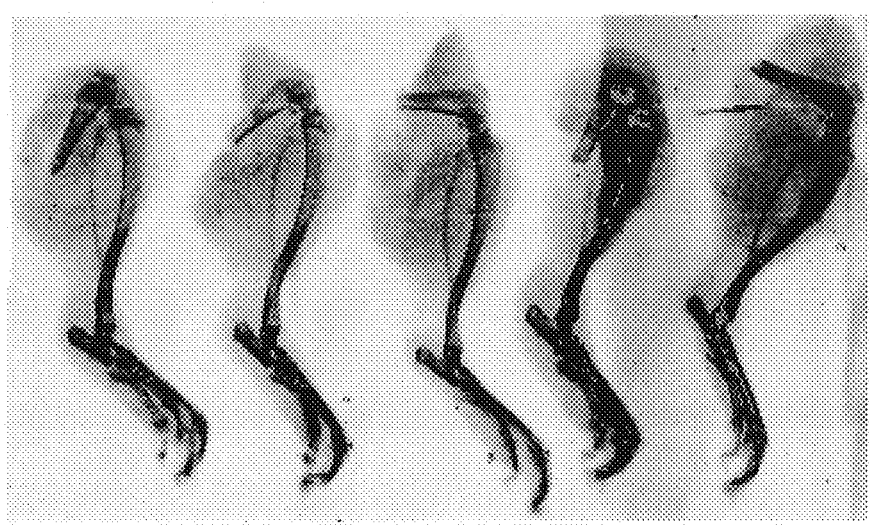
FIG. 6C is soft X-ray photographs of hind limbs in Comparative Example 9-2.
Figure 7:
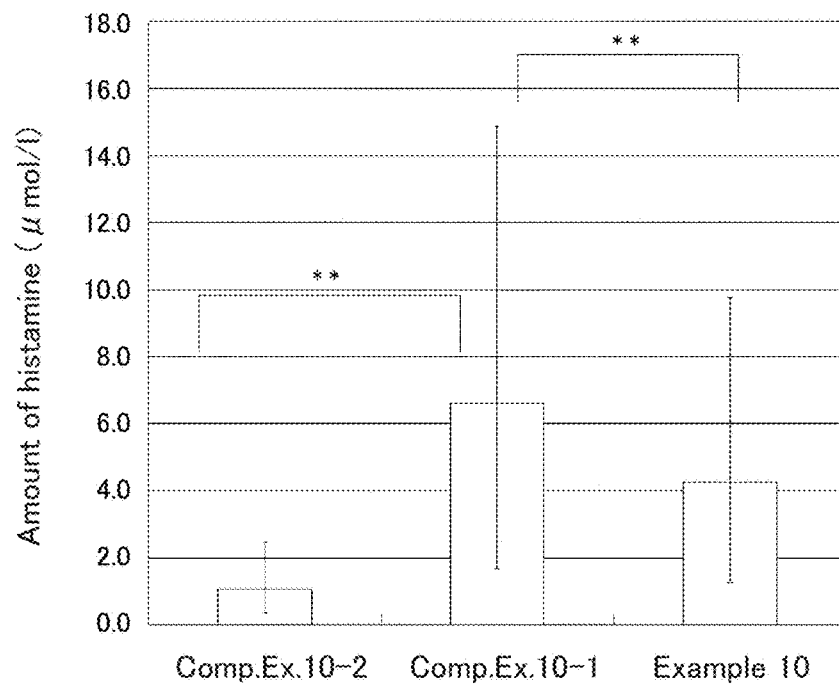
FIG. 7 is a graph showing the respective average values of amounts of histamine in sera of Example 10 and Comparative Examples 10-1 and 10-2.

Measurement results of the volumes of edemas in Example 8 and Comparative Examples 8-1 and 8-2 are shown in a graph of FIG. 4. In the graph of FIG. 4, the vertical axis indicates an average value (ml) of the volumes of edemas. As shown in FIG. 4, the volume of an edema in Comparative Example 8-1 (untreated group) was 0.35 ml, the volume of an edema in Comparative Example 8-2 (group of administering no bacterial cell) was 0.95 ml, and the volume of an edema in Example 8 was 0.63 ml. Thus, an increase in volume of edema was suppressed in Example 8 of administering the bacterial cell powder as compared with that in Comparative Example 8-2 of administering no bacterial cell powder. That is, the bacterial cell powder exerted anti-allergic properties to allergic reactions caused by intradermal immunization. Moreover, in Example 8, even though 10 mg/kg, p.o. of the bacterial cell powder was administered once a day for 2 weeks, adverse effects were not found.

Example 9

In the present example, an oral administration test of a bacterial cell powder prepared in the same manner as in Example 1, using rats with adjuvant arthritis, being rheumatoid arthritis models was conducted as follows. Then effects of the bacterial cell powder on rheumatoid arthritis (autoimmune disease) were evaluated.

First, 0.6 mg of *Mycobacterium tuberculosis* (*M. buturicum*, Lot 0640-33, produced by Difco) was suspended in 0.1 ml of liquid paraffin (produced by Hoei Kagaku). Thus, a complete adjuvant was prepared. In the oral administration test, 5 of 5-week-old male Wistar rats (purchased from Japan SLC, Inc., 150 to 160 g) were used. 0.1 ml of adjuvant was inoculated into each of hind footpads of the rats. 20 mg/kg, p.o. of the bacterial cell powder was administered once a day for 21 days from the day of the inoculation. Then volumes of edemas generated on the respective footpads were measured on 3rd day, 17th day, and 21st day from the day of the inoculation using Volume Meter MK-550 (produced by MLTROMACHI KIKAI CO., LTD.), and each average value was calculated. Moreover, a tarsal bone, a metatarsal bone, and a knucklebone in hindlimb of each of the rats were photographed on the 3rd day, the 17th day, and the 21st day using a soft X-ray apparatus, and images of bone lesions caused by adjuvant arthritis were morphologically observed.

Comparative Example 9-1

As an untreated group of the present example, an oral administration test was conducted in the same manner as in Example 9 except that the bacterial cell powder was not administered. Then volumes of edemas were measured, an average value of the volumes was calculated, and a morphological observation was conducted.

Comparative Example 9-2

As a positive control group of the present example, an oral administration test was conducted in the same manner as in Example 9 except that 0.1 mg/kg, p.o. of indomethacin (produced by Sigma-Aldrich Corporation) that is an anti-inflammatory agent was administered as substitute for the bacterial cell powder. Then volumes of edemas were measured, an average value of the volumes was calculated, and a morphological observation was conducted.

Measurement results of the volumes of edemas in Example 9 and Comparative Examples 9-1 and 9-2 are shown in a graph of FIG. 5. In the graph of FIG. 5, the vertical axis indicates an average value (ml) of the volumes of edemas, and the horizontal axis indicates the number of days (day) after the inoculation. The respective bars show the respective results of Comparative Example 9-1, Example 9, and Comparative Example 9-2, starting from the left. As shown in FIG. 5, compared with increases in the volumes of edemas on the 17th day and the 21st day from the day of the inoculation in Comparative Example 9-1 (untreated group), those in Example 9 (group of administering the bacterial cell powder) were suppressed as well as those in Comparative Example 9-2 (positive control group). That is, as compared with edema formation caused by adjuvant arthritis in Comparative Example 9-1 of administering no bacterial cell powder, that in Example 9 of administering the bacterial cell powder was suppressed as well as that in Comparative Example 9-2 of administering indomethacin.

The images of bone lesions in hindlimbs in Example 9 and Comparative Examples 9-1 and 9-2 are shown in photographs of FIGS. 6A, 6B, and 6C. FIG. 6A is photographs of Example 9, FIG. 6B is a photograph of Comparative Example 9-1, and FIG. 6C is photographs of Comparative Example 9-2. As shown in FIG. 6B, bone lesions (parts indicated by arrows) caused by adjuvant arthritis were observed in Comparative Example 9-1 (untreated group). In contrast, as shown in FIGS. 6A and 6C, inflammations and bone lesions caused by adjuvant arthritis were suppressed in Example 9 of administering the bacterial cell powder as well as those in Comparative Example 9-2 of administering indomethacin. As described above, it was considered that the bacterial cell powder of the present invention is useful in preventing and/or ameliorating autoimmune diseases such as chronic rheumatoid arthritis and the like. Moreover, in Example 9, even though 20 mg/kg, p.o. of the bacterial cell powder was administered once a day for 21 days, adverse effects were not found.

Example 10

In the present example, an oral administration test of a bacterial cell powder prepared in the same manner as in Example 1, using model mice with allergic reactions caused by egg albumin was conducted as follows. Then effects of the bacterial cell powder on releasing histamine in the allergic reactions were evaluated.

The bacterial cell powder was administered, an egg albumin/aluminum hydroxide gel was prepared and administered, and blood was collected in the same manner as in the measurement of the amount of IgE in a serum of Example 7 except that 19 of 4-week-old female BALB/c mice (purchased from Japan SLC, Inc.) were used. Then sera were collected from the blood thus collected, and amounts of histamine in the sera were measured in accordance with a protocol of histamine ELISA Kit (produced by Immunotech), and an average value of the amounts of histamine was calculated.

Comparative Example 10-1

In the present example, an oral administration test was conducted in the same manner as in Example 10 except that 15 of the mice were used, and the bacterial cell powder was not orally administered. Then amounts of histamine in sera were measured, and an average value of the amounts of histamine caused by egg albumin was calculated.

Comparative Example 10-2

In the present example, an oral administration test was conducted in the same manner as in Example 10 except that 13 of the mice were used, and the egg albumin/aluminum hydroxide gel and the bacterial cell powder were not orally administered. Then amounts of histamine in sera were measured, and an average value of the amounts of histamine was calculated.

The respective average values of the amounts of histamin in sera of Example 10 and Comparative Examples 10-1 and 10-2 were shown in FIG. 7 and Table 15 below. As shown in FIG. 7 and Table 15, the amount of histamin was reduced in Example 10 of administering the bacterial cell powder as compared with that in Comparative Example 10-1 of administering no bacterial cell powder. As described above, it was confirmed that a release of histamin was suppressed by administering the bacterial cell powder.

TABLE 15

| Example | Histamine amount (μmol/l) |
|---|---|
| Example 10 | 4.25 |
| Comp. Ex. 10-1 | 6.60 |
| Comp. Ex. 10-2 | 1.06 |

Example 11

In the present example, stamina enhancement effects and anti-fatigue effects of a bacterial cell powder prepared in the same manner as in Example 1 were evaluated.

4-week-old male ddY mice (purchased from Japan SLC, Inc.) were subjected to a suspension as follows, so that mice with a time of maintaining suspending from 40 to 60 seconds were selected. The suspension was conducted as follows. First, the mice were suspended by their forefeet from a bar for suspending, being arranged horizontally under the state where each of the mice was weighted by adding a load of 10% by weight of its weight to its hind foot. Then the time (seconds) of maintaining suspending was measured.

The bacterial cell powder was dissolved in a saline solution for injection so that a resultant sample has a concentration of the bacterial cell powder of 1 mg/ml. Thus, a sample was prepared. 0.1 ml of the sample per 10 g of the weight of each of the mice was orally administered into each of selected 10 mice once a day for 10 days so that the administration amount of the sample became 10 mg/kg, p.o./day.

After 11 days from the administration of the sample, time of maintaining suspending was measured by the suspension. This measurement was a first measurement. After 30 minutes from the first measurement, time of maintaining suspending was again measured by the suspension. This measurement was a second measurement.

Comparative Example 11

In the present example, an oral administration and a measurement of time of maintaining suspending by a suspension were conducted in the same manner as in Example 11 except that the bacterial cell powder was not orally administered.

Figure 8:
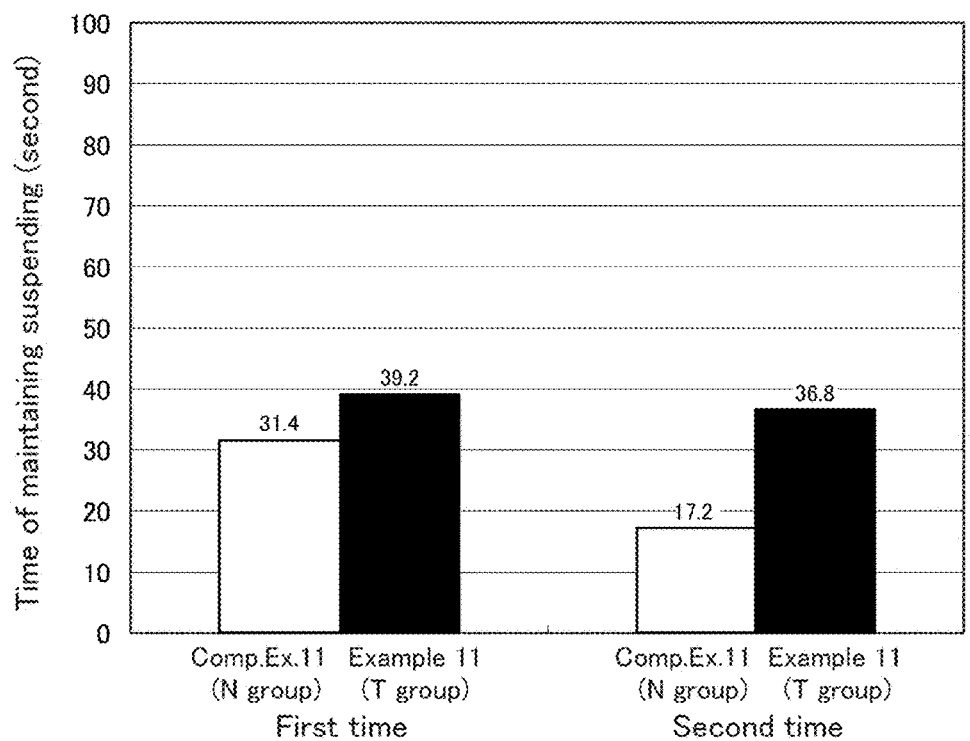
FIG. 8 is a graph showing measurement results obtained by a suspension of Example 11.

A graph of measurement results of the time of maintaining suspending in Example 11 and Comparative Example 11 are shown in FIG. 8. In the graph of FIG. 8, the vertical axis indicates the time (seconds) of maintaining suspending, and the horizontal axis indicates the first measurement result and the second measurement result, starting from the left. In the graph of FIG. 8, white bars indicate measurement results of Comparative Example 11 (N group), and black bars indicate measurement results of Example 11 (T group).

As shown in FIG. 8, in Example 11 (T group) of administering the sample for 10 days, the first time of maintaining suspending was 39.2 seconds, and in Comparative Example 11 (N group), it was 31.4 seconds. That is, the first time of maintaining suspending in Example 11 was 1.2 times longer than that in Comparative Example 11. In the second measurement, the time of maintaining suspending in Example 11 (T group) was 36.8 seconds, and it was 17.2 seconds in Comparative Example 11 (N group). That is, in the second measurement, the time of maintaining suspending in Example 11 was 2.1 times longer than that in Comparative Example 11, and the difference between them was significant ($P=0.0034$). As described above, stamina enhancement effects and anti-fatigue effects were exerted by orally administering the sample containing the bacterial cell powder for 10 days.

Example 12

In the present example, an oral administration and a measurement of time of maintaining suspending by a suspension were conducted in the same manner as in Example 11 except that an administration period of the sample containing the bacterial cell powder was 20 days.

Comparative Example 12

In the present example, an oral administration and a measurement of time of maintaining suspending by a suspension were conducted in the same manner as in Example 12 except that the bacterial cell powder was not orally administered.

Figure 9:
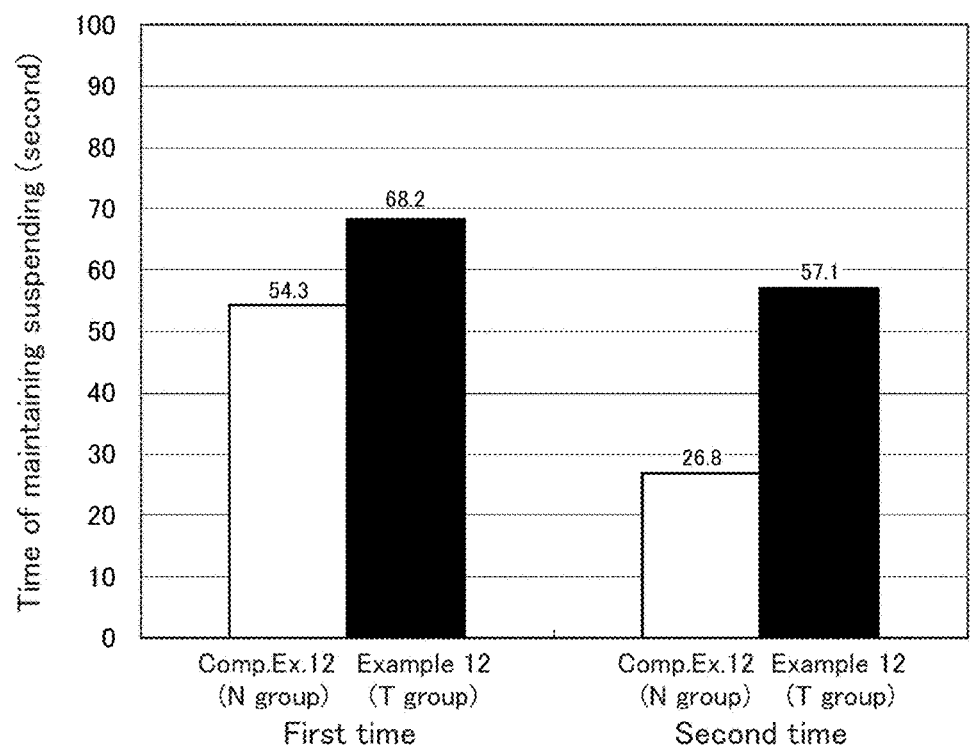
FIG. 9 is a graph showing measurement results obtained by a suspension of Example 12.

A graph of measurement results of the time of maintaining suspending in Example 12 and Comparative Example 12 are shown in FIG. 9. In the graph of FIG. 9, the vertical axis indicates the time (seconds) of maintaining suspending, and the horizontal axis indicates the first measurement result and the second measurement result, starting from the left. In the graph of FIG. 9, white bars indicate measurement results of Comparative Example 12 (N group), and black bars indicate measurement results of Example 12 (T group).

As shown in FIG. 9, in Example 12 (T group) of administering the sample for 20 days, the first time of maintaining suspending was 68.2 seconds, and in Comparative Example 12 (N group), it was 54.3 seconds. That is, the first time of maintaining suspending in Example 12 was 1.2 times longer than that in Comparative Example 12. In the second measurement, the time of maintaining suspending in Example 12 (T group) was 57.1 seconds, and it was 26.8 seconds in Comparative Example 12 (N group). That is, in the second measurement, the time of maintaining suspending in Example 12 was 2.1 times longer than that in Comparative Example 12, and the difference between them was significant ($P=0.0001$). As described above, stamina enhancement effects and anti-fatigue effects were exerted by orally administering the sample containing the bacterial cell powder for 20 days.

As will be noted from Examples 1 to 10 and Comparative Examples 1 to 10, by ingesting the purple non-sulfur bacteria of the present invention, ulcer formation, inflammatory cell invasion, and swelling of a mucosal epithelium in a large bowel were suppressed, and regeneration of an epithelium was accelerated, and an inflammatory disease was prevented and/or ameliorated. By ingesting the purple non-sulfur bacteria of the present invention, centrilobular hepatic necrosis and inflammatory cell invasion in a liver were suppressed, and an inflammatory disease was prevented. By ingesting the purple non-sulfur bacteria of the present invention, amounts of IgE and histamine in a serum were reduced, secretion of Th2 cytokine was suppressed, a Th1/Th2 imbalance was ameliorated, and an allergy was suppressed. By ingesting the purple non-sulfur bacteria of the present invention, an allergic reaction caused by intradermal immunization was suppressed, and an autoimmune disease was prevented and/or ameliorated. Moreover, as will be noted from Examples 11 and 12 and Comparative Examples 11 and 12, by ingesting the purple non-sulfur bacteria of the present invention, stamina is enhanced, and fatigue was suppressed. The purple non-sulfur bacteria of the present invention does not have adverse effects caused by ingesting it for a long term and thus showed high safety.

INDUSTRIAL APPLICABILITY

As described above, the purple non-sulfur bacteria of the present invention has various effects of suppressing ulcer formation, suppressing inflammatory cell invasion, suppressing swelling of a mucosal epithelium, regenerating an epithelium, suppressing hepatic necrosis, accelerating swelling of liver cell, reducing amounts of IgE and histamine in a serum, suppressing Th2 cytokine secretion, ameliorating a Th1/Th2 imbalance, suppressing an allergic reaction, suppressing an autoimmune disease, enhancing stamina, anti-fatigue, and the like. The purple non-sulfur bacteria of the present invention can prevent and/or ameliorate at least one disease selected from the group consisting of inflammatory diseases, allergic diseases, and autoimmune diseases, can enhance stamina, and can suppress fatigue. The purple non-sulfur bacteria of the present invention has high safety, so that it can be administered for the purpose of preventing diseases, and also, it can be administered for a long term. Thus, according to the present invention, a preventive and/or ameliorative agent, a stamina enhancement agent, an anti-fatigue agent, a pharmaceutical, and food and drink, being useful in preventing and/or ameliorating at least one disease selected from the group consisting of inflammatory diseases, allergic diseases, and autoimmune diseases, enhancing stamina, and anti-fatigue and having high safety, can be provided, and application ranges thereof are not limited and wide.

The invention claimed is:

1. A method for ameliorating at least one condition, the method comprising the step of:

administering to a subject in need thereof an effective amount of an ameliorative agent comprising at least one of a purple non-sulfur bacteria and a culture material obtained by culturing the purple non-sulfur bacteria, wherein the condition is at least one selected from the group consisting of liver injury and egg albumin allergy, and the purple non-sulfur bacteria comprises *Rhodobacter azotoformans* BP0899 strain (Accession No. NITE BP-644).

* * * * *

SEQUENCE LISTING

```
<160> NUMBER OF SEQ ID NOS: 9

<210> SEQ ID NO 1
<211> LENGTH: 1427
<212> TYPE: DNA
<213> ORGANISM: Rhodobacter azotoformans

<400> SEQUENCE: 1
gagtttgatc ctggctcaga atgaacgctg gcggcaggcc taacacatgc aagtcgagcg      60
aagtcttcgg acttagcggc ggacgggtga gtaacgcgtg ggaacatgcc caaaggtacg     120
gaatagcccc gggaaactgg gagtaatacc gtatgtgccc ttcgggggaa agatttatcg     180
cctttggatt ggcccgcgtt ggattaggta gttggtgggg taatggccta ccaagccgac     240
gatccatagc tggtttgaga ggatgatcag ccacactggg actgagacac ggcccagact     300
cctacgggag gcagcagtgg ggaatcttag acaatgggcg caagcctgat ctagccatgc     360
cgcgtgatcg atgaaggcct tagggttgta aagatctttc aggtgggaag ataatgacgg     420
taccaccaga agaagccccg gctaactccg tgccagcagc cgcggtaata cggaggggc     480 tagcgttatt cggaattact gggcgtaaag cgcacgtagg cggactggaa agtcaggggt     540
gaaatcccgg ggctcaaccc cggaactgcc tttgaaactc ccagtcttga ggtcgagaga     600
ggtgagtgga attccgagtg tagaggtgaa attcgtagat attcggagga acaccagtgg     660
cgaaggcggc tcactggctc gatactgacg ctgaggtgcg aaagcgtggg agcaaacag     720 gattagatac cctggtagtc cacgccgtaa acgatgaatg ccagtcgtcg ggcagcatgc     780
tgttcggtga cacacctaac ggattaagca ttccgcctgg ggagtacggc cgcaaggtta     840
aaactcaaag gaattgacgg gggcccgcac aagcggtgga gcatgtggtt taattcgaag     900
caacgcgcag aaccttacca acccttgaca tggcgatcgc ggttccagag atggttcctt     960
cagttcggct ggatcgcaca caggtgctgc atggctgtcg tcagctcgtg tcgtgagatg    1020
ttcggttaag tccggcaacg agcgcaaccc acgtcctcag ttgccagcat tcagttgggc    1080
actctgggga aactgccggt gataagccgg aggaaggtgt ggatgacgtc aagtcctcat    1140
ggcccttacg ggttgggcta cacacgtgct acaatggcag tgacaatggg ttaatcccaa    1200
aaagctgtct cagttcggat tggggtctgc aactcgaccc catgaagtcg gaatcgctag    1260
taatcgcgta acagcatgac gcggtgaata cgttcccggg ccttgtacac accgcccgtc    1320
acaccatggg aattggttct acccgaaggc ggtgcgccaa cctcgcaaga ggaggcagcc    1380
gaccacggta ggatcagtga ctggggtgaa gtcgtaacaa ggtagcc                  1427

<210> SEQ ID NO 2
<211> LENGTH: 19
<212> TYPE: DNA
<213> ORGANISM: Artificial
<220> FEATURE:
<223> OTHER INFORMATION: a primer
```

<400> SEQUENCE: 2
gagtttgatc ctggctcag                                                19

<210> SEQ ID NO 3
<211> LENGTH: 19
<212> TYPE: DNA
<213> ORGANISM: Artificial
<220> FEATURE:
<223> OTHER INFORMATION: a primer

<400> SEQUENCE: 3
ctcctacggg aggcagcag                                                19

<210> SEQ ID NO 4
<211> LENGTH: 21
<212> TYPE: DNA
<213> ORGANISM: Artificial
<220> FEATURE:
<223> OTHER INFORMATION: a primer

<400> SEQUENCE: 4
ggattagata ccctggtagt c                                             21

<210> SEQ ID NO 5
<211> LENGTH: 16
<212> TYPE: DNA
<213> ORGANISM: Artificial
<220> FEATURE:
<223> OTHER INFORMATION: a primer

<400> SEQUENCE: 5
gcaacgagcg caaccc                                                   16

<210> SEQ ID NO 6
<211> LENGTH: 18
<212> TYPE: DNA
<213> ORGANISM: Artificial
<220> FEATURE:
<223> OTHER INFORMATION: a primer

<400> SEQUENCE: 6
gtattaccgc ggctgctg                                                 18

<210> SEQ ID NO 7
<211> LENGTH: 18
<212> TYPE: DNA
<213> ORGANISM: Artificial
<220> FEATURE:
<223> OTHER INFORMATION: a primer

<400> SEQUENCE: 7
taccagggta tctaatcc                                                 18

<210> SEQ ID NO 8
<211> LENGTH: 16
<212> TYPE: DNA
<213> ORGANISM: Artificial
<220> FEATURE:
<223> OTHER INFORMATION: a primer

<400> SEQUENCE: 8
ccattgtagc acgtgt                                                   16

<210> SEQ ID NO 9

```
<211> LENGTH: 17
<212> TYPE: DNA
<213> ORGANISM: Artificial
<220> FEATURE:
<223> OTHER INFORMATION: a primer

<400> SEQUENCE: 9
aaggaggtga tccagcc                                                    17
```